United States Patent
Jardetzky et al.

(10) Patent No.: US 8,927,695 B2
(45) Date of Patent: Jan. 6, 2015

(54) PROTEIN-BASED ASSAYS FOR SCREENING OF THE IGE-RECEPTOR INTERACTION

(75) Inventors: Theodore S Jardetzky, Palo Alto, CA (US); Beomkyu Kim, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 826 days.

(21) Appl. No.: 13/074,543

(22) Filed: Mar. 29, 2011

(65) Prior Publication Data

US 2011/0281365 A1 Nov. 17, 2011

Related U.S. Application Data

(60) Provisional application No. 61/341,580, filed on Mar. 30, 2010.

(51) Int. Cl.
*C07K 16/00* (2006.01)
*C07K 16/42* (2006.01)

(52) U.S. Cl.
CPC .............. *C07K 16/4291* (2013.01); *C07K 16/00* (2013.01); *C07K 2317/526* (2013.01); *C07K 2317/528* (2013.01); *G01N 2500/02* (2013.01); *Y10S 530/862* (2013.01); *Y10S 530/866* (2013.01)
USPC ..................... 530/387.1; 530/350; 530/387.3; 530/391.5; 530/862; 530/866; 435/7.1

(58) Field of Classification Search
None
See application file for complete search history.

(56) References Cited

U.S. PATENT DOCUMENTS

| | | | |
|---|---|---|---|
| 5,945,294 A | 8/1999 | Frank et al. | |
| 6,889,145 B1 * | 5/2005 | Jardetzky et al. | ............... 702/27 |
| 7,855,275 B2 | 12/2010 | Eigenbrot et al. | |

OTHER PUBLICATIONS

Wurzburg et al., J Mol Biol. Oct. 16, 2009;393(1)1 76-90. doi: 10.1016/j.jmb.2009.08.012. Epub Aug. 13, 2009.*
Wan et al., Nat Immunol. Jul. 2002;3(7):681-6. Epub Jun. 17, 2002.*
Young et al., Protein Eng. Feb. 1995;8(2):193-9.*
Kamiya et al., Tohoku J Exp Med. Dec. 1996;180(4):297-308.*
Nissim et al. (1991) Mapping of the high affinity Fc epsilon receptor binding site to the third constant region domain of IgE. Embo J 10:101-107.
Basu et al. (1993) Purification and characterization of human recombinant IgE-Fc fragments that bind to the human high affinity IgE receptor. J. Biol. Chem. 268:13118-13127.
Presta et al. (1994) A conformational rearrangement upon binding of IgE to its high affinity receptor. J. Biol. Chem. 269:26368-26373.
Henry et al. (1997) Participation of the N-terminal region of Cepsilon3 in the binding of human IgE to its high-affinity receptor FcepsilonRI. Biochemistry 36:15568-15578.
Wurzburg et al. (2000) Structure of the human IgE-Fc C epsilon 3-C epsilon 4 reveals conformational flexibility in the antibody effector domains. Immunity 13:375-385.
Garman et al. (2000) Structure of the Fc fragment of human IgE bound to its high-affinity receptor Fc epsilonRI alpha. Nature 406:259-266.
Wurzburg et al. (2009) Conformational flexibility in immunoglobulin E-Fc 3-4 revealed in multiple crystal forms. J. Mol. Biol. 393(1):176-190.
Wan et al. (2002) The crystal structure of IgE Fc reveals an asymmetrically bent conformation. Nat. Immunol. 3(7):681-686.
Sechi et al. (1996) A Conformational Rearrangement upon Binding of IgE to Its High Affinity Receptor. J. Biol. Chem. 271:19256-19263.
Young et al. (1995) Secretion of recombinant human IgE-Fc by mammalian cells and biological activity of glycosylation site mutants. Protein Eng. 8(2):193-199.

* cited by examiner

*Primary Examiner* — Michael Szperka
(74) *Attorney, Agent, or Firm* — Jenny Buchbinder

(57) ABSTRACT

Embodiments of the invention are related to a polypeptide comprising the amino acid sequence of a human IgE-Fc Cε3-Cε4, wherein said Cε3-Cε4 starts at amino acid 328 and ends at amino acid 547 of said IgE-Fc, and wherein C 328 is A and K 367 is C. Other embodiments concern a second polypeptide comprising the amino acid sequence of a human FcεRIα extracellular region, wherein said extracellular region starts at amino acid 1 and ends at amino acid 176 of said FcεRIα. Still other embodiments are related to a method of identifying a compound that inhibits the binding of an IgE-Fc to a FcεRIα, said method comprising: contacting the polypeptide, wherein said IgE-Fc Cε3-Cε4 sequence is labeled with a fluorophore, and the second polypeptide, with a test compound; and determining whether binding of said polypeptide to said second polypeptide is decreased in the presence of said test compound.

21 Claims, 14 Drawing Sheets

| Sites for Fluorescent Dye Labeling in the IgE-Fc | | | |
|---|---|---|---|
| Residue | $C\alpha$-$C\alpha$ distances | | $\Delta$ distance |
| | Closed | Open | |
| 367 (K) | 35Å | 50Å | 15Å |
| 369 (T) | 37Å | 50Å | 13Å |
| 427 (R) | 21Å | 36Å | 15Å |

FIG. 1D

< DNA sequences of Wild-type and C328A-K367C IgE-Fc >

Wild-type IgE-Fc (C3-C4) – Cystein at 328 from Baculo_construct

GCGGATCCCTGTGCAGATTCGAACCCGAGAGGGGTGAGCGCCTACCTAAGCCGGC
CCAGCCCGTTCGACCTGTTCATCCGCAAGTCGCCCACGATCACCTGTCTGGTGGTGG
ACCTGGCACCCAGCAAGGGGACCGTGAACCTGACCTGGTCCCGGGCCAGTGGGAA
GCCTGTGAACCACTCCACCAGAAAGGAGGAGAAGCAGCGCAATGGCACGTTAACCG
TCACGTCCACCCTGCCGGTGGGCACCCGAGACTGGATCGAGGGGGAGACCTACCAG
TGCAGGGTGACCCACCCCACCTGCCCAGGGCCCTCATGCGGTCCACGACCAAGAC
CAGCGGCCCGCGTGCTGCCCCGGAAGTCTATGCGTTTGCGACGCCGGAGTGGCCGG
GGAGCCGGGACAAGCGCACCCTCGCCTGCCTGATCCAGAACTTCATGCCTGAGGAC
ATCTCGGTGCAGTGGCTGCACAACGAGGTGCAGCTCCCGGACGCCCGGCACAGCAC
GACGCAGCCCCGCAAGACCAAGGGCTCCGGCTTCTTCGTCTTCAGCCGCCTGGAGGT
GACCAGGGCCGAATGGGAGCAGAAAGATGAGTTCATCTGCCGTGCAGTCCATGAGG
CAGCGAGCCCCTCACAGACCGTCCAGCGAGCGGTGTCTGTAAATCCCGGTAAA

C328A-K367C IgE-Fc (C3-C4) – Cystein at 367 by using BaculoDirect C-term linear DNA GCGGATCCCGCTGCAGATTCGAACCCGAGAGGGGTGAGCGCCTACCTAAGCCGGC
CCAGCCCGTTCGACCTGTTCATCCGCAAGTCGCCCACGATCACCTGTCTGGTGGTGG
ACCTGGCACCCAGCTGTGGGACCGTGAACCTGACCTGGTCCCGGGCCAGTGGGAA
GCCTGTGAACCACTCCACCAGAAAGGAGGAGAAGCAGCGCAATGGCACGTTAACCG
TCACGTCCACCCTGCCGGTGGGCACCCGAGACTGGATCGAGGGGGAGACCTACCAG
TGCAGGGTGACCCACCCCACCTGCCCAGGGCCCTCATGCGGTCCACGACCAAGAC
CAGCGGCCCGCGTGCTGCCCCGGAAGTCTATGCGTTTGCGACGCCGGAGTGGCCGG
GGAGCCGGGACAAGCGCACCCTCGCCTGCCTGATCCAGAACTTCATGCCTGAGGAC
ATCTCGGTGCAGTGGCTGCACAACGAGGTGCAGCTCCCGGACGCCCGGCACAGCAC
GACGCAGCCCCGCAAGACCAAGGGCTCCGGCTTCTTCGTCTTCAGCCGCCTGGAGGT
GACCAGGGCCGAATGGGAGCAGAAAGATGAGTTCATCTGCCGTGCAGTCCATGAGG
CAGCGAGCCCCTCACAGACCGTCCAGCGAGCGGTGTCTGTAAATCCCGGTAAA-
*GCTGCTGATGACGACGACAAGCGATATCTAGACCCAGCTTTCTTGTACAAAGTGGTGAGA*
*ATGAATGAAGATCTGGGGAAGCCTATCCCTAACCCTCTCCTCGGTCTCGATTCTACGCGTA*
*CCGGTCATCATCACCATCACCATTGA* – additional DNA sequences of the mutant encoding amino acids for several tags.

FIG. 8A

< Comparison of DNA sequences of wt and mutant >

```
wt        1   GCGGATCCCTGTGCAGATTCGAACCCGAGAGGGGTGAGCGCCTACCTAAGCCGGCCCAGC
mutant,   1   GCGGATCCCCCTGCAGATTCGAACCCGAGAGGGGTGAGCGCCTACCTAAGCCGGCCCAGC
              *******  *********************************************** wt       61   CCGTTCGACCTGTTCATCCGCAAGTCGCCCACGATCACCTGTCTGGTGGTGGACCTGGCA
mutant,  61   CCGTTCGACCTGTTCATCCGCAAGTCGCCCACGATCACCTGTCTGGTGGTGGACCTGGCA
              ************************************************************ wt      121   CCCAGCAAGGGGACCGTGAACCTGACCTGGTCCCGGGCCAGTGGGAAGCCTGTGAACCAC
mutant, 121   CCCAGCTGTGGGACCGTGAACCTGACCTGGTCCCGGGCCAGTGGGAAGCCTGTGAACCAC
              ****  ************************************************** wt      181   TCCACCAGAAAGGAGGAGAAGCAGCGCAATGGCACGTTAACCGTCACGTCCACCCTGCCG
mutant, 181   TCCACCAGAAAGGAGGAGAAGCAGCGCAATGGCACGTTAACCGTCACGTCCACCCTGCCG
              ************************************************************ wt      241   GTGGGCACCCGAGACTGGATCGAGGGGGAGACCTACCAGTGCAGGGTGACCCACCCCCAC
mutant, 241   GTGGGCACCCGAGACTGGATCGAGGGGGAGACCTACCAGTGCAGGGTGACCCACCCCCAC
              ************************************************************ wt      301   CTGCCCAGGGCCCTCATGCGGTCCACGACCAAGACCAGCGGCCCGCGTGCTGCCCCGGAA
mutant, 301   CTGCCCAGGGCCCTCATGCGGTCCACGACCAAGACCAGCGGCCCGCGTGCTGCCCCGGAA
              ************************************************************ wt      361   GTCTATGCGTTTGCGACGCCGGAGTGGCCGGGGAGCCGGGACAAGCGCACCCTCGCCTGC
mutant, 361   GTCTATGCGTTTGCGACGCCGGAGTGGCCGGGGAGCCGGGACAAGCGCACCCTCGCCTGC
              ************************************************************ wt      421   CTGATCCAGAACTTCATGCCTGAGGACATCTCGGTGCAGTGGCTGCACAACGAGGTGCAG
mutant, 421   CTGATCCAGAACTTCATGCCTGAGGACATCTCGGTGCAGTGGCTGCACAACGAGGTGCAG
              ************************************************************ wt      481   CTCCCGGACGCCCGGCACAGCACGACGCAGCCCCGCAAGACCAAGGGCTCCGGCTTCTTC
mutant, 481   CTCCCGGACGCCCGGCACAGCACGACGCAGCCCCGCAAGACCAAGGGCTCCGGCTTCTTC
              ************************************************************ wt      541   GTCTTCAGCCGCCTGGAGGTGACCAGGGCCGAATGGGAGCAGAAAGATGAGTTCATCTGC
mutant, 541   GTCTTCAGCCGCCTGGAGGTGACCAGGGCCGAATGGGAGCAGAAAGATGAGTTCATCTGC
              ************************************************************ wt      601   CGTGCAGTCCATGAGGCAGCGAGCCCCTCACAGACCGTCCAGCGAGCGGTGTCTGTAAAT
mutant, 601   CGTGCAGTCCATGAGGCAGCGAGCCCCTCACAGACCGTCCAGCGAGCGGTGTCTGTAAAT
              ************************************************************ wt      661   CCCGGTAAA
mutant, 661   CCCGGTAAA
              *********
```

FIG. 8B

< Amino acid sequences of Wild-type and C328A-K367C IgE-Fc >

Wild-type IgE-Fc (C3-C4) – Cystein at 328 from Baculo_construct

```
         10         20         30         40         50         60
ADPCADSNPR GVSAYLSRPS PFDLFIRKSP TITCLVVDLA PSKGTVNLTW SRASGKPVNH 70         80         90        100        110        120
STRKEEKQRN GTLTVTSTLP VGTRDWIEGE TYQCRVTHPH LPRALMRSTT KTSGPRAAPE 130        140        150        160        170        180
VYAFATPEWP GSRDKRTLAC LIQNFMPEDI SVQWLHNEVQ LPDARHSTTQ PRKTKGSGFF 190        200        210        220
VFSRLEVTRA EWEQKDEFIC RAVHEAASPS QTVQRAVSVN PGK
```

C328A-K367C IgE-Fc (C3-C4) – Cystein at 367 by using BaculoDirect C-term linear DNA

```
         10         20         30         40         50         60
ADPAADSNPR GVSAYLSRPS PFDLFIRKSP TITCLVVDLA PSCGTVNLTW SRASGKPVNH 70         80         90        100        110        120
STRKEEKQRN GTLTVTSTLP VGTRDWIEGE TYQCRVTHPH LPRALMRSTT KTSGPRAAPE 130        140        150        160        170        180
VYAFATPEWP GSRDKRTLAC LIQNFMPEDI SVQWLHNEVQ LPDARHSTTQ PRKTKGSGFF 190        200        210        220        230        240
VFSRLEVTRA EWEQKDEFIC RAVHEAASPS QTVQRAVSVN PGKAADDDDK RYLDPAFLYK 250        260        270
VVRMNEDLGK PIPNPLLGLD STRTGHHHHH H  (coming from the C-term linear DNA)
```

< Comparison of WT and Mutant >

```
WT       1 ADPCADSNPRGVSAYLSRPSPFDLFIRKSPTITCLVVDLAPSKGTVNLTWSRASGKPVNH
Mutant   1 ADPAADSNPRGVSAYLSRPSPFDLFIRKSPTITCLVVDLAPSCGTVNLTWSRASGKPVNH
           *** ***************************************  ***************

WT      61 STRKEEKQRNGTLTVTSTLPVGTRDWIEGETYQCRVTHPHLPRALMRSTTKTSGPRAAPE
Mutant  61 STRKEEKQRNGTLTVTSTLPVGTRDWIEGETYQCRVTHPHLPRALMRSTTKTSGPRAAPE
           ************************************************************

WT     121 VYAFATPEWPGSRDKRTLACLIQNFMPEDISVQWLHNEVQLPDARHSTTQPRKTKGSGFF
Mutant 121 VYAFATPEWPGSRDKRTLACLIQNFMPEDISVQWLHNEVQLPDARHSTTQPRKTKGSGFF
           ************************************************************

WT     181 VFSRLEVTRAEWEQKDEFICRAVHEAASPSQTVQRAVSVNPGK
Mutant 181 VFSRLEVTRAEWEQKDEFICRAVHEAASPSQTVQRAVSVNPGK
           ******************************************
```

FIG. 8C

4B11 Kappa.pseq

1  MSVPTQVLGLLLLWLTGARCDIQLTQSPASLSASVGETVTITCRTSENIYSYLAWFQQRQ
   61  GKSPHLLVYDSKILAEGVSSRFSGSGSGTQFSLEINSLQPEDFGTYYCQHHYGIPLTFGA
  121  GTKLELKRADAAPTVSIFPPSSEQLTSGGASVVCFLNNFYPKDINVKWKIDGSERQNGVL
  181  NSWTDQDSKDSTYSMSSTLTLTKDEYERHNSYTCEATHKTSTSPIVKSFNRNEC

4B11 Kappa-seq.

ATGAGTGTGCCCACTCAGGTCCTGGGGTTGCTGCTGCTGTGGCTTACAGGTGCCAGATGTGACATCCAGTTG
ACTCAGTCTCCAGCCTCCCTATCTGCATCTGTGGGAGAAACTGTCACCATCACATGTCGAACAAGTGAAAAT
ATTTACAGTTATTTAGCATGGTTTCAGCAGAGGCAGGGAAAATCTCCTCACCTCCTAGTCTATGACTCAAAA
ATCCTAGCAGAGGGTGTGTCATCAAGGTTCAGTGGCAGTGGATCAGGCACACAGTTTTCTCTGGAGATCAAT
AGCCTGCAGCCTGAAGATTTTGGGACTTATTACTGTCAACATCATTATGGTATTCCGCTCACGTTCGGTGCT
GGGACCAAGTTGGAGCTGAAACGGGCTAATGCTGCACCAACTGCATCCATCTTCCCACCATCCAGTGAGCAG
TTAACATCTGGAGGTGCCTCAGTCGTGTGCTTCTTGAACAACTTCTACCCCAAAGACATCAATGTCAAGTGG
AAGATTGATGGCAGTGAACGACAAAATGGCGTCCTGAACAGTTGGACTGATCAGGACAGCAAAGACAGCACC
TACAGCATGAGCAGCACCCTCACGTTGACCAAGGACGAGTATGAACGACATAACAGCTATACCTGTGAGGCC
ACTCACAAGACATCAACTTCACCCATTGTCAAGAGCTTCAACAGGAATGAGTGT

Translated seq.

1    M   S   V   P   T   Q   V   L   G   L   L   L   L   W   T   G   A   R   C
    1   ATGAGTGTGCCCACTCAGGTCCTGGGGTTGCTGCTGCTGTGGCTTACAGGTGCCAGATGT

21    D   I   Q   L   T   Q   S   P   A   S   L   S   A   S   V   G   E   T   V   T
   61   GACATCCAGTTGACTCAGTCTCCAGCCTCCCTATCTGCATCTGTGGGAGAAACTGTCACC

41    I   T   C   R   T   S   E   N   I   Y   S   Y   L   A   W   F   Q   Q   R   Q
  121   ATCACATGTCGAACAAGTGAAAATATTTACAGTTATTTAGCATGGTTTCAGCAGAGGCAG

61    G   K   S   P   H   L   L   V   Y   D   S   K   I   L   A   E   G   V   S   S
  181   GGAAAATCTCCTCACCTCCTAGTCTATGACTCAAAAATCCTAGCAGAGGGTGTGTCATCA

81    R   F   S   G   S   G   S   G   T   Q   F   S   L   E   I   N   S   L   Q   P
  241   AGGTTCAGTGGCAGTGGATCAGGCACACAGTTTTCTCTGGAGATCAATAGCCTGCAGCCT

101    E   D   F   G   T   Y   Y   C   Q   H   H   Y   G   I   P   L   T   F   G   A
  301   GAAGATTTTGGGACTTATTACTGTCAACATCATTATGGTATTCCGCTCACGTTCGGTGCT

121    G   T   K   L   E   L   K   R   A   N   A   A   P   T   A   S   I   F   P   P
  361   GGGACCAAGTTGGAGCTGAAACGGGCTAATGCTGCACCAACTGCATCCATCTTCCCACCA

141    S   S   E   Q   L   T   S   G   G   A   S   V   V   C   F   L   N   N   F   Y
  421   TCCAGTGAGCAGTTAACATCTGGAGGTGCCTCAGTCGTGTGCTTCTTGAACAACTTCTAC

161    P   K   D   I   N   V   K   W   K   I   D   G   S   E   R   Q   N   G   V   L
  481   CCCAAAGACATCAATGTCAAGTGGAAGATTGATGGCAGTGAACGACAAAATGGCGTCCTG

181    N   S   W   T   D   Q   D   S   K   D   S   T   Y   S   M   S   S   T   L   T
  541   AACAGTTGGACTGATCAGGACAGCAAAGACAGCACCTACAGCATGAGCAGCACCCTCACG

201    L   T   K   D   E   Y   E   R   H   N   S   Y   T   C   E   A   T   H   K   T
  601   TTGACCAAGGACGAGTATGAACGACATAACAGCTATACCTGTGAGGCCACTCACAAGACA

221    S   T   S   P   I   V   K   S   F   N   R   N   E   C
  661   TCAACTTCACCCATTGTCAAGAGCTTCAACAGGAATGAGTGT

FIG. 9A

4B11-heavy chain-pseq.

```
  1 MNLELSWIFLVTLLNGIQSEVKLVESGGELVQPGESLRLSCSTSGFTFTDYYMSWVRQPP
 61 GKALEWLGFIRNKANSYTTEYSTSVKGRFYISRDDSQNILYLQMNTLRPEDGATYYCVRN
121 KKVYYYAVDYWGQGTSVTVSSAKTTPPSVYPLAPGSAAQTNSMVTLGCLVKGYFPEPVTV
181 TWNSGSLSSGVHTFPAVLQSDLYTLSSSVTVPSSTWPSETVTCNVAHPASSTKVDKKIVP
241 RDCGCKPCICTVPEVSSVFIF
```

4B11-heavy chain-seq.

ATGAACTTGGAGCTCAGCTGGATTTTCCTTGTAACACTTTTAAATGGTATCCA
GAGTGAGGTGAAACTGGTGGAGTCTGGGGGAGAATTGGTTCAGCCTGGGGA
ATCTCTGAGACTCTCCTGCTCAACTTCTGGGTTCACCTTCACGGATTACTATAT
GAGTTGGGTCCGCCAGCCTCCAGGAAAGGCACTTGAATGGTTGGGTTTTATT
AGAAACAAAGCTAATAGTTACACAACAGAGTACAGTACATCTGTAAAGGGTC
GGTTTTACATCTCCAGAGATGATTCCCAAAACATCCTCTACCTTCAAATGAAC
ACCCTGAGACCTGAGGACGGCGCCACTTATTACTGTGTAAGAAATAAAAAG
TATACTACTATGCTGTGGACTACTGGGGTCAAGGGACCTCAGTCACCGTCTCC
TCAGCCAAAACGACACCCCCATCTGTCTATCCACTGGCCCCTGGATCTGCTGC
CCAAACTAACTCCATGGTGACCCTGGGATGCCTGGTCAAGGGCTATTTCCCTG
AGCCAGTGACAGTGACCTGGAACTCTGGATCCCTGTCCAGCGGTGTGCACAC
CTTCCCAGCTGTCCTGCAGTCTGACCTCTACACTCTGAGCAGCTCAGTGACTG
TCCCCTCCAGCACCTGGCCCAGCGAGACCGTCACCTGCAACGTTGCCCACCC
GGCCAGCAGCACCAAGGTGGACAAGAAAATTGTGCCCAGGGATTGTGGTTGT
AAGCCTTGCATATGTACAGTCCCAGAAGTA

FIG. 9B

Translated Seq.

```
  1 M  N  L  E  L  S  W  I  F  L  V  T  L  L  N  G  I  Q  S  E
  1 ATGAACTTGGAGCTCAGCTGGATTTTCCTTGTAACACTTTTAAATGGTATCCAGAGTGAG

21 V  K  L  V  E  S  G  G  E  L  V  Q  P  G  E  S  L  R  L  S
 61 GTGAAACTGGTGGAGTCTGGGGGAGAATTGGTTCAGCCTGGGGAATCTCTGAGACTCTCC

41 C  S  T  S  G  F  T  F  T  D  Y  Y  M  S  W  V  R  Q  P  P
121 TGCTCAACTTCTGGGTTCACCTTCACGGATTACTATATGAGTTGGGTCCGCCAGCCTCCA

61 G  K  A  L  E  W  L  G  F  I  R  N  K  A  N  S  Y  T  T  E
181 GGAAAGGCACTTGAATGGTTGGGTTTTATTAGAAACAAAGCTAATAGTTACACAACAGAG

81 Y  S  T  S  V  K  G  R  F  Y  I  S  R  D  D  S  Q  N  I  L
241 TACAGTACATCTGTAAAGGGTCGGTTTTACATCTCCAGAGATGATTCCCAAAACATCCTC

101 Y  L  Q  M  N  T  L  R  P  E  D  G  A  T  Y  Y  C  V  R  N
301 TACCTTCAAATGAACACCCTGAGACCTGAGGACGGCGCCACTTATTACTGTGTAAGAAAT

121 K  K  V  Y  Y  Y  A  V  D  Y  W  G  Q  G  T  S  V  T  V  S
361 AAAAAAGTATACTACTATGCTGTGGACTACTGGGGTCAAGGGACCTCAGTCACCGTCTCC

141 S  A  K  T  T  P  P  S  V  Y  P  L  A  P  G  S  A  A  Q  T
421 TCAGCCAAAACGACACCCCCATCTGTCTATCCACTGGCCCCTGGATCTGCTGCCCAAACT

161 N  S  M  V  T  L  G  C  L  V  K  G  Y  F  P  E  P  V  T  V
481 AACTCCATGGTGACCCTGGGATGCCTGGTCAAGGGCTATTTCCCTGAGCCAGTGACAGTG

181 T  W  N  S  G  S  L  S  S  G  V  H  T  F  P  A  V  L  Q  S
541 ACCTGGAACTCTGGATCCCTGTCCAGCGGTGTGCACACCTTCCCAGCTGTCCTGCAGTCT

201 D  L  Y  T  L  S  S  S  V  T  V  P  S  S  T  W  P  S  E  T
601 GACCTCTACACTCTGAGCAGCTCAGTGACTGTCCCCTCCAGCACCTGGCCCAGCGAGACC

221 V  T  C  N  V  A  H  P  A  S  S  T  K  V  D  K  K  I  V  P
661 GTCACCTGCAACGTTGCCCACCCGGCCAGCAGCACCAAGGTGGACAAGAAAATTGTGCCC

241 R  D  C  G  C  K  P  C  I  C  T  V  P  E  V
721 AGGGATTGTGGTTGTAAGCCTTGCATATGTACAGTCCCAGAAGTA
```

FIG. 9C

SEQUENCE LISTING

```
<160> NUMBER OF SEQ ID NOS: 15

<210> SEQ ID NO 1
<211> LENGTH: 816
<212> TYPE: DNA
<213> ORGANISM: Artificial Sequence
<220> FEATURE:
<223> OTHER INFORMATION: C328A-K367C IgE-Fc (C3-C4) mutant: Cystein at
      367 by using BaculoDirect C-term linear DNA
<220> FEATURE:
<221> NAME/KEY: exon
<222> LOCATION: (1)..(816)

<400> SEQUENCE: 1 gcg gat ccc gct gca gat tcg aac ccg aga ggg gtg agc gcc tac cta       48
Ala Asp Pro Ala Ala Asp Ser Asn Pro Arg Gly Val Ser Ala Tyr Leu
1               5                  10                  15 agc cgg ccc agc ccg ttc gac ctg ttc atc cgc aag tcg ccc acg atc       96
Ser Arg Pro Ser Pro Phe Asp Leu Phe Ile Arg Lys Ser Pro Thr Ile
            20                  25                  30 acc tgt ctg gtg gtg gac ctg gca ccc agc tgt ggg acc gtg aac ctg      144
Thr Cys Leu Val Val Asp Leu Ala Pro Ser Cys Gly Thr Val Asn Leu
        35                  40                  45 acc tgg tcc cgg gcc agt ggg aag cct gtg aac cac tcc acc aga aag      192
Thr Trp Ser Arg Ala Ser Gly Lys Pro Val Asn His Ser Thr Arg Lys
    50                  55                  60 gag gag aag cag cgc aat ggc acg tta acc gtc acg tcc acc ctg ccg      240
Glu Glu Lys Gln Arg Asn Gly Thr Leu Thr Val Thr Ser Thr Leu Pro
65                  70                  75                  80 gtg ggc acc cga gac tgg atc gag ggg gag acc tac cag tgc agg gtg      288
Val Gly Thr Arg Asp Trp Ile Glu Gly Glu Thr Tyr Gln Cys Arg Val
                85                  90                  95
```

```
acc cac ccc cac ctg ccc agg gcc ctc atg cgg tcc acg acc aag acc      336
Thr His Pro His Leu Pro Arg Ala Leu Met Arg Ser Thr Thr Lys Thr
            100                 105                 110 agc ggc ccg cgt gct gcc ccg gaa gtc tat gcg ttt gcg acg ccg gag      384
Ser Gly Pro Arg Ala Ala Pro Glu Val Tyr Ala Phe Ala Thr Pro Glu
        115                 120                 125 tgg ccg ggg agc cgg gac aag cgc acc ctc gcc tgc ctg atc cag aac      432
Trp Pro Gly Ser Arg Asp Lys Arg Thr Leu Ala Cys Leu Ile Gln Asn
130                 135                 140 ttc atg cct gag gac atc tcg gtg cag tgg ctg cac aac gag gtg cag      480
Phe Met Pro Glu Asp Ile Ser Val Gln Trp Leu His Asn Glu Val Gln
145                 150                 155                 160 ctc ccg gac gcc cgg cac agc acg acg cag ccc cgc aag acc aag ggc      528
Leu Pro Asp Ala Arg His Ser Thr Thr Gln Pro Arg Lys Thr Lys Gly
                165                 170                 175 tcc ggc ttc ttc gtc ttc agc cgc ctg gag gtg acc agg gcc gaa tgg      576
Ser Gly Phe Phe Val Phe Ser Arg Leu Glu Val Thr Arg Ala Glu Trp
            180                 185                 190 gag cag aaa gat gag ttc atc tgc cgt gca gtc cat gag gca gcg agc      624
Glu Gln Lys Asp Glu Phe Ile Cys Arg Ala Val His Glu Ala Ala Ser
        195                 200                 205 ccc tca cag acc gtc cag cga gcg gtg tct gta aat ccc ggt aaa gct      672
Pro Ser Gln Thr Val Gln Arg Ala Val Ser Val Asn Pro Gly Lys Ala
210                 215                 220 gct gat gac gac gac aag cga tat cta gac cca gct ttc ttg tac aaa      720
Ala Asp Asp Asp Asp Lys Arg Tyr Leu Asp Pro Ala Phe Leu Tyr Lys
225                 230                 235                 240 gtg gtg aga atg aat gaa gat ctg ggg aag cct atc cct aac cct ctc      768
Val Val Arg Met Asn Glu Asp Leu Gly Lys Pro Ile Pro Asn Pro Leu
                245                 250                 255 ctc ggt ctc gat tct acg cgt acc ggt cat cat cac cat cac cat tga      816
Leu Gly Leu Asp Ser Thr Arg Thr Gly His His His His His His
            260                 265                 270

<210> SEQ ID NO 2
<211> LENGTH: 669
<212> TYPE: DNA
<213> ORGANISM: Homo sapiens
<220> FEATURE:
<221> NAME/KEY: exon
<222> LOCATION: (1)..(669)

<400> SEQUENCE: 2 gcg gat ccc tgt gca gat tcg aac ccg aga ggg gtg agc gcc tac cta       48
Ala Asp Pro Cys Ala Asp Ser Asn Pro Arg Gly Val Ser Ala Tyr Leu
1               5                   10                  15 agc cgg ccc agc ccg ttc gac ctg ttc atc cgc aag tcg ccc acg atc       96
Ser Arg Pro Ser Pro Phe Asp Leu Phe Ile Arg Lys Ser Pro Thr Ile
            20                  25                  30 acc tgt ctg gtg gtg gac ctg gca ccc agc aag ggg acc gtg aac ctg      144
Thr Cys Leu Val Val Asp Leu Ala Pro Ser Lys Gly Thr Val Asn Leu
        35                  40                  45 acc tgg tcc cgg gcc agt ggg aag cct gtg aac cac tcc acc aga aag      192
Thr Trp Ser Arg Ala Ser Gly Lys Pro Val Asn His Ser Thr Arg Lys
50                  55                  60 gag gag aag cag cgc aat ggc acg tta acc gtc acg tcc acc ctg ccg      240
Glu Glu Lys Gln Arg Asn Gly Thr Leu Thr Val Thr Ser Thr Leu Pro
65                  70                  75                  80 gtg ggc acc cga gac tgg atc gag ggg gag acc tac cag tgc agg gtg      288
Val Gly Thr Arg Asp Trp Ile Glu Gly Glu Thr Tyr Gln Cys Arg Val
                85                  90                  95
```

```
acc cac ccc cac ctg ccc agg gcc ctc atg cgg tcc acg acc aag acc      336
Thr His Pro His Leu Pro Arg Ala Leu Met Arg Ser Thr Thr Lys Thr
            100                 105                 110 agc ggc ccg cgt gct gcc ccg gaa gtc tat gcg ttt gcg acg ccg gag      384
Ser Gly Pro Arg Ala Ala Pro Glu Val Tyr Ala Phe Ala Thr Pro Glu
        115                 120                 125 tgg ccg ggg agc cgg gac aag cgc acc ctc gcc tgc ctg atc cag aac      432
Trp Pro Gly Ser Arg Asp Lys Arg Thr Leu Ala Cys Leu Ile Gln Asn
    130                 135                 140 ttc atg cct gag gac atc tcg gtg cag tgg ctg cac aac gag gtg cag      480
Phe Met Pro Glu Asp Ile Ser Val Gln Trp Leu His Asn Glu Val Gln
145                 150                 155                 160 ctc ccg gac gcc cgg cac agc acg acg cag ccc cgc aag acc aag ggc      528
Leu Pro Asp Ala Arg His Ser Thr Thr Gln Pro Arg Lys Thr Lys Gly
                165                 170                 175 tcc ggc ttc ttc gtc ttc agc cgc ctg gag gtg acc agg gcc gaa tgg      576
Ser Gly Phe Phe Val Phe Ser Arg Leu Glu Val Thr Arg Ala Glu Trp
            180                 185                 190 gag cag aaa gat gag ttc atc tgc cgt gca gtc cat gag gca gcg agc      624
Glu Gln Lys Asp Glu Phe Ile Cys Arg Ala Val His Glu Ala Ala Ser
        195                 200                 205 ccc tca cag acc gtc cag cga gcg gtg tct gta aat ccc ggt aaa          669
Pro Ser Gln Thr Val Gln Arg Ala Val Ser Val Asn Pro Gly Lys
    210                 215                 220
```

<210> SEQ ID NO 3
<211> LENGTH: 270
<212> TYPE: PRT
<213> ORGANISM: Artificial Sequence
<220> FEATURE:
<223> OTHER INFORMATION: C328A-K367C IgE-Fc (C3-C4) mutant: Cystein at
      367 by using BaculoDirect C-term linear DNA
<220> FEATURE:
<221> NAME/KEY: PEPTIDE
<222> LOCATION: (1)..(270)

<400> SEQUENCE: 3

```
Ala Asp Pro Ala Ala Asp Ser Asn Pro Arg Gly Val Ser Ala Tyr Leu
1               5                   10                  15

Ser Arg Pro Ser Pro Phe Asp Leu Phe Ile Arg Lys Ser Pro Thr Ile
            20                  25                  30

Thr Cys Leu Val Val Asp Leu Ala Pro Ser Cys Gly Thr Val Asn Leu
        35                  40                  45

Thr Trp Ser Arg Ala Ser Gly Lys Pro Val Asn His Ser Thr Arg Lys
    50                  55                  60

Glu Glu Lys Gln Arg Asn Gly Thr Leu Thr Val Thr Ser Thr Leu Pro
65                  70                  75                  80

Val Gly Thr Arg Asp Trp Ile Glu Gly Glu Thr Tyr Gln Cys Arg Val
                85                  90                  95

Thr His Pro His Leu Pro Arg Ala Leu Met Arg Ser Thr Thr Lys Thr
            100                 105                 110

Ser Gly Pro Arg Ala Ala Pro Glu Val Tyr Ala Phe Ala Thr Pro Glu
        115                 120                 125

Trp Pro Gly Ser Arg Asp Lys Arg Thr Leu Ala Cys Leu Ile Gln Asn
    130                 135                 140

Phe Met Pro Glu Asp Ile Ser Val Gln Trp Leu His Asn Glu Val Gln
145                 150                 155                 160

Leu Pro Asp Ala Arg His Ser Thr Thr Gln Pro Arg Lys Thr Lys Gly
                165                 170                 175
```

```
Ser Gly Phe Phe Val Phe Ser Arg Leu Glu Val Thr Arg Ala Glu Trp
        180                 185                 190

Glu Gln Lys Asp Glu Phe Ile Cys Arg Ala Val His Glu Ala Ala Ser
            195                 200                 205

Pro Ser Gln Thr Val Gln Arg Ala Val Ser Val Asn Pro Gly Lys Ala
    210                 215                 220

Ala Asp Asp Asp Lys Arg Tyr Leu Asp Pro Ala Phe Leu Tyr Lys
225                 230                 235                 240

Val Arg Met Asn Glu Asp Leu Gly Lys Pro Ile Pro Asn Pro Leu Leu
                245                 250                 255

Gly Leu Asp Ser Thr Arg Thr Gly His His His His His His
            260                 265                 270

<210> SEQ ID NO 4
<211> LENGTH: 223
<212> TYPE: PRT
<213> ORGANISM: Homo sapiens
<220> FEATURE:
<221> NAME/KEY: PEPTIDE
<222> LOCATION: (1)..(223)
<223> OTHER INFORMATION: Wildtype IgE-Fc (C3-C4)

<400> SEQUENCE: 4

Ala Asp Pro Cys Ala Asp Ser Asn Pro Arg Gly Val Ser Ala Tyr Leu
1               5                   10                  15

Ser Arg Pro Ser Pro Phe Asp Leu Phe Ile Arg Lys Ser Pro Thr Ile
            20                  25                  30

Thr Cys Leu Val Val Asp Leu Ala Pro Ser Lys Gly Thr Val Asn Leu
        35                  40                  45

Thr Trp Ser Arg Ala Ser Gly Lys Pro Val Asn His Ser Thr Arg Lys
    50                  55                  60

Glu Glu Lys Gln Arg Asn Gly Thr Leu Thr Val Thr Ser Thr Leu Pro
65                  70                  75                  80

Val Gly Thr Arg Asp Trp Ile Glu Gly Glu Thr Tyr Gln Cys Arg Val
                85                  90                  95

Thr His Pro His Leu Pro Arg Ala Leu Met Arg Ser Thr Thr Lys Thr
            100                 105                 110

Ser Gly Pro Arg Ala Ala Pro Glu Val Tyr Ala Phe Ala Thr Pro Glu
        115                 120                 125

Trp Pro Gly Ser Arg Asp Lys Arg Thr Leu Ala Cys Leu Ile Gln Asn
    130                 135                 140

Phe Met Pro Glu Asp Ile Ser Val Gln Trp Leu His Asn Glu Val Gln
145                 150                 155                 160

Leu Pro Asp Ala Arg His Ser Thr Thr Gln Pro Arg Lys Thr Lys Gly
                165                 170                 175

Ser Gly Phe Phe Val Phe Ser Arg Leu Glu Val Thr Arg Ala Glu Trp
            180                 185                 190

Glu Gln Lys Asp Glu Phe Ile Cys Arg Ala Val His Glu Ala Ala Ser
        195                 200                 205

Pro Ser Gln Thr Val Gln Arg Ala Val Ser Val Asn Pro Gly Lys
    210                 215                 220

<210> SEQ ID NO 5
<211> LENGTH: 42
<212> TYPE: DNA
<213> ORGANISM: Artificial Sequence
<220> FEATURE:
```

-continued

```
<223> OTHER INFORMATION: V5 epitope Tag
<220> FEATURE:
<221> NAME/KEY: Unsure
<222> LOCATION: (1)..(42)
<223> OTHER INFORMATION: V5 epitope tag

<400> SEQUENCE: 5
gggaagccta tccctaaccc tctcctcggt ctcgattcta cg                         42

<210> SEQ ID NO 6
<211> LENGTH: 14
<212> TYPE: PRT
<213> ORGANISM: Artificial Sequence
<220> FEATURE:
<223> OTHER INFORMATION: V5 epitope Tag
<220> FEATURE:
<221> NAME/KEY: peptide
<222> LOCATION: (1)..(14)
<223> OTHER INFORMATION: V5 epitope Tag

<400> SEQUENCE: 6

Gly Lys Pro Ile Pro Asn Pro Leu Leu Gly Leu Asp Ser Thr
1               5                   10

<210> SEQ ID NO 7
<211> LENGTH: 702
<212> TYPE: DNA
<213> ORGANISM: Mus musculus
<220> FEATURE:
<221> NAME/KEY: Unsure
<222> LOCATION: (1)..(702)
<223> OTHER INFORMATION: light chain of the 4B11-B8 FAb

<400> SEQUENCE: 7
atgagtgtgc ccactcaggt cctggggttg ctgctgctgt ggcttacagg tgccagatgt       60
gacatccagt tgactcagtc tccagcctcc ctatctgcat ctgtgggaga aactgtcacc      120
atcacatgtc gaacaagtga aaatatttac agttatttag catggtttca gcagaggcag      180
ggaaaatctc ctcacctcct agtctatgac tcaaaaatcc tagcagaggg tgtgtcatca      240
aggttcagtg gcagtggatc aggcacacag ttttctctgg agatcaatag cctgcagcct      300
gaagattttg ggacttatta ctgtcaacat cattatggta ttccgctcac gttcggtgct      360
gggaccaagt tggagctgaa acgggctaat gctgcaccaa ctgcatccat cttcccacca      420
tccagtgagc agttaacatc tggaggtgcc tcagtcgtgt gcttcttgaa caacttctac      480
cccaaagaca tcaatgtcaa gtggaagatt gatggcagtg aacgacaaaa tggcgtcctg      540
aacagttgga ctgatcagga cagcaaagac agcacctaca gcatgagcag cacccttacg      600
ttgaccaagg acgagtatga acgacataac agctatacct gtgaggccac tcacaagaca      660
tcaacttcac ccattgtcaa gagcttcaac aggaatgagt gt                         702

<210> SEQ ID NO 8
<211> LENGTH: 234
<212> TYPE: PRT
<213> ORGANISM: Mus musculus
<220> FEATURE:
<221> NAME/KEY: peptide
<222> LOCATION: (1)..(234)
<223> OTHER INFORMATION: light chain of the 4B11-B8 FA

<400> SEQUENCE: 8

Met Ser Val Pro Thr Gln Val Leu Gly Leu Leu Leu Leu Trp Leu Thr
1               5                   10                  15

Gly Ala Arg Cys Asp Ile Gln Leu Thr Gln Ser Pro Ala Ser Leu Ser
```

```
                   20                  25                  30
Ala Ser Val Gly Glu Thr Val Thr Ile Thr Cys Arg Thr Ser Glu Asn
            35                  40                  45

Ile Tyr Ser Tyr Leu Ala Trp Phe Gln Gln Arg Gln Gly Lys Ser Pro
        50                  55                  60

His Leu Leu Val Tyr Asp Ser Lys Ile Leu Ala Glu Gly Val Ser Ser
65                  70                  75                  80

Arg Phe Ser Gly Ser Gly Ser Gly Thr Gln Phe Ser Leu Glu Ile Asn
                85                  90                  95

Ser Leu Gln Pro Glu Asp Phe Gly Thr Tyr Tyr Cys Gln His His Tyr
            100                 105                 110

Gly Ile Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 9
<211> LENGTH: 765
<212> TYPE: DNA
<213> ORGANISM: Mus musculus
<220> FEATURE:
<221> NAME/KEY: Unsure
<222> LOCATION: (1)..(765)
<223> OTHER INFORMATION: heavy chain of the 4B11-B8 FAb

<400> SEQUENCE: 9

```
atgaacttgg agctcagctg gattttcctt gtaacacttt taaatggtat ccagagtgag    60
gtgaaactgg tggagtctgg gggagaattg gttcagcctg gggaatctct gagactctcc   120
tgctcaactt ctgggttcac cttcacggat tactatatga gttgggtccg ccagcctcca   180
ggaaaggcac ttgaatggtt gggttttatt agaaacaaag ctaatagtta cacaacagag   240
tacagtacat ctgtaaaggg tcggttttac atctccagag atgattccca aaacatcctc   300
taccttcaaa tgaacaccct gagacctgag gacggcgcca ttattactg tgtaagaaat   360
aaaaaagtat actactatgc tgtggactac tggggtcaag gacctcagt caccgtctcc    420
tcagccaaaa cgacaccccc atctgtctat ccactggccc ctggatctgc tgcccaaact   480
aactccatgg tgaccctggg atgcctggtc aagggctatt tccctgagcc agtgacagtg   540
acctggaact ctggatccct gtccagcggt gtgcacacct tcccagctgt cctgcagtct   600
gacctctaca ctctgagcag ctcagtgact gtcccctcca gcacctggcc cagcgagacc   660
gtcacctgca acgttgccca cccggccagc agcaccaagg tggacaagaa aattgtgccc   720
agggattgtg gttgtaagcc ttgcatatgt acagtcccag aagta              765
```

<210> SEQ ID NO 10
<211> LENGTH: 261
<212> TYPE: PRT
<213> ORGANISM: Mus musculus
<220> FEATURE:
<221> NAME/KEY: PEPTIDE
<222> LOCATION: (1)..(261)
<223> OTHER INFORMATION: heavy chain of the 4B11-B8 FAb

<400> SEQUENCE: 10

Met Asn Leu Glu Leu Ser Trp Ile Phe Leu Val Thr Leu Leu Asn Gly
1               5                   10                  15

Ile Gln Ser Glu Val Lys Leu Val Glu Ser Gly Gly Glu Leu Val Gln
            20                  25                  30

Pro Gly Glu Ser Leu Arg Leu Ser Cys Ser Thr Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Leu Gly Phe Ile Arg Asn Lys Ala Asn Ser Tyr Thr Thr Glu
65                  70                  75                  80

Tyr Ser Thr Ser Val Lys Gly Arg Phe Tyr Ile Ser Arg Asp Asp Ser
                85                  90                  95

Gln Asn Ile Leu Tyr Leu Gln Met Asn Thr Leu Arg Pro Glu Asp Gly
            100                 105                 110

Ala Thr Tyr Tyr Cys Val Arg Asn Lys Lys Val Tyr Tyr Ala Val
        115                 120                 125

Asp Tyr Trp Gly Gln Gly Thr Ser Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
    210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe
            260

<210> SEQ ID NO 11
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(33)
<223> OTHER INFORMATION: primer to create K367C substitution

<400> SEQUENCE: 11
gacctggcac ccagctgtgg gaccgtgaac ctg         33

<210> SEQ ID NO 12
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(33)
<223> OTHER INFORMATION: primer to create T369C substitution

<400> SEQUENCE: 12
gcacccagca aggggtgtgt gaacctgacc tgg                33

<210> SEQ ID NO 13
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(33)
<223> OTHER INFORMATION: primer to create R427 substitution

<400> SEQUENCE: 13
cacccccacc tgccctgtgc cctcatgcgc tcc                33

<210> SEQ ID NO 14
<211> LENGTH: 547
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid

<400> SEQUENCE: 14

Xaa Val Gln Leu Val Gln Ser Gly Ala Glu Val Arg Lys Pro Gly Ala
1               5                   10                  15

Ser Val Arg Val Ser Cys Lys Ala Ser Gly Tyr Thr Phe Ile Asp Ser
            20                  25                  30

Tyr Val Gly Trp Ile Arg Gln Ala Pro Gly His Gly Leu Glu Trp Ile
        35                  40                  45

His Trp Ile Asn Pro Asn Ser Gly Gly Thr Asn Tyr Ala Pro Arg Phe
    50                  55                  60

Gln Gly Arg Val Thr Met Thr Arg Asp Ala Ser Phe Ser Thr Ala Tyr
65                  70                  75                  80

Met Asp Leu Arg Ser Leu Arg Ser Asp Asp Ser Ala Val Phe Tyr Cys
                85                  90                  95

Ala Lys Ser Asx Pro Phe Trp Ser Asx Tyr Asx Phe Asx Tyr Ser Ser
            100                 105                 110

Ser Glx Glx Gly Thr Glu Val Thr Tyr Thr Val Ser Gly Ala Trp Thr
        115                 120                 125

Leu Pro Xaa Val Phe Pro Leu Thr Arg Cys Cys Lys Asx Ile Pro Ser
    130                 135                 140

Asn Ala Thr Ser Val Thr Leu Gly Cys Leu Ala Thr Gly Tyr Phe Pro
145                 150                 155                 160

Glu Pro Val Met Val Thr Trp Asx Thr Gly Ser Leu Asn Gly Thr Thr

```
                165                 170                 175
Leu Pro Ala Thr Thr Leu Thr Leu Ser Gly His Tyr Ala Thr Ile Ser
            180                 185                 190
Leu Leu Thr Val Ser Gly Ala Trp Ala Lys Gln Met Phe Thr Cys Arg
            195                 200                 205
Val Ala His Thr Pro Ser Ser Thr Val Asx Asn Lys Thr Phe Ser Val
            210                 215                 220
Cys Ser Arg Asp Phe Thr Pro Pro Thr Val Lys Ile Leu Glx Ser Ser
225                 230                 235                 240
Cys Asx Gly Leu Gly His Phe Pro Pro Thr Ile Glx Leu Cys Leu Val
                245                 250                 255
Ser Gly Tyr Thr Pro Gly Thr Ile Asn Ile Thr Trp Leu Glx Asx Gly
                260                 265                 270
Glx Val Met Asp Val Asp Leu Ser Thr Ala Ser Thr Glu Ser Gln Gly
            275                 280                 285
Glu Leu Ala Ser Thr Glu Ser Gln Leu Thr Leu Ser Gln Lys His Trp
            290                 295                 300
Leu Ser Asp Arg Thr Tyr Thr Cys Gln Val Thr Tyr Gln Gly His Thr
305                 310                 315                 320
Phe Gln Asp Ser Thr Lys Lys Cys Ala Asp Ser Asn Pro Arg Gly Val
                325                 330                 335
Ser Ala Tyr Leu Ser Arg Pro Ser Pro Phe Asp Leu Phe Ile Arg Lys
                340                 345                 350
Ser Pro Thr Ile Thr Cys Leu Val Val Asp Leu Ala Pro Ser Lys Gly
                355                 360                 365
Thr Val Asn Leu Thr Trp Ser Arg Ala Ser Gly Lys Pro Val Asn His
            370                 375                 380
Ser Thr Arg Lys Glu Glu Lys Gln Arg Asn Gly Thr Leu Thr Val Thr
385                 390                 395                 400
Ser Thr Leu Pro Val Gly Thr Arg Asp Trp Ile Glu Gly Glu Thr Tyr
                405                 410                 415
Gln Cys Arg Val Thr His Pro His Leu Pro Arg Ala Leu Met Arg Ser
                420                 425                 430
Thr Thr Lys Thr Ser Gly Pro Arg Ala Ala Pro Glu Val Tyr Ala Phe
            435                 440                 445
Ala Thr Pro Glu Trp Pro Gly Ser Arg Asp Lys Arg Thr Leu Ala Cys
            450                 455                 460
Leu Ile Gln Asn Phe Met Pro Glu Asp Ile Ser Val Gln Trp Leu His
465                 470                 475                 480
Asn Glu Val Gln Leu Pro Asp Ala Arg His Ser Thr Thr Gln Pro Arg
                485                 490                 495
Lys Thr Lys Gly Ser Gly Phe Phe Val Phe Ser Arg Leu Glu Val Thr
                500                 505                 510
Arg Ala Glu Trp Gln Glu Lys Asp Glu Phe Ile Cys Arg Ala Val His
            515                 520                 525
Glu Ala Ala Ser Pro Ser Gln Thr Val Gln Arg Ala Val Ser Val Asn
            530                 535                 540
Pro Gly Lys
545

<210> SEQ ID NO 15
<211> LENGTH: 257
<212> TYPE: PRT
<213> ORGANISM: Homo sapiens
```

```
<400> SEQUENCE: 15

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                      70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn
```

PROTEIN-BASED ASSAYS FOR SCREENING OF THE IGE-RECEPTOR INTERACTION

CROSS-REFERENCE TO RELATED APPLICATIONS

This application claims the benefit of U.S. Provisional Application No. 61/341,580, filed Mar. 30, 2010, which is incorporated herein by reference.

STATEMENT REGARDING GOVERNMENT SUPPORT

This invention was made with Government support under contract R37AI18939 awarded by NIH/NIAID. The Government has certain rights in this invention.

INCORPORATION OF SEQUENCE LISTING

A computer readable form of the sequence listing, "SeqListing_ASB_043TRA_UTL_ST25.txt", 21 kilo bytes, created on Jul. 26, 2011, submitted via EFS-WEB, is herein incorporated by reference.

BACKGROUND OF THE INVENTION

1. Field of the Invention

The field of the invention is measuring processes involving non-membrane antibody-receptor binding, compositions therefore; and processes of forming such compositions.

2. Description of Related Art

The interaction of IgE antibodies with the high affinity IgE receptor, FcεRI, is a critical step in most allergic reactions. The IgE-receptor interaction has been well studied and targeted in the search for treatments for allergic diseases (Wiegand, T. W. et al. 1996 *J Immunol* 157: 221-230; Nakamura, G. R. et al. 2001 *Biochemistry* 40: 9828-9835; Stamos, J. et. al. 2004 *Structure* 12: 1289-1301; Chang, T. W. 2000 *Nat Biotechnol* 18: 157-162; Mirkina, I., Schweighoffer, T. & Kricek, F. 2007 *Immunol Lett* 109: 120-128). However, outside of the anti-IgE antibody Omalizumab, there are no compounds that have been identified and approved for the treatment of patients with severe allergies that interfere with the receptor binding. The identification of novel inhibitors of IgE antibody binding to its receptor would therefore represent a significant step forward in developing new approaches to treating allergy and asthma.

Allergic diseases have become the most common immune system disorder, affecting 10~40% of the population in industrialized countries (Meltzer, E. O. & Grant, J. A. 1999 *Ann Allergy Asthma Immunol* 83: 455-463; Crater, S. E. & Platts-Mills, T. A. 1998 *Curr Opin Pediatr* 10: 594-599). Most allergic diseases are triggered by IgE-mediated hypersensitivity reactions (Kraft, S. & Kinet, J.P. 2007 *Nat Rev Immunol* 7: 365-378). While the primary function of IgE antibodies is to mediate immune response protection to foreign antigens, the overproduction of IgE antibodies to normally benign environmental stimuli, such as dust mites, pet dander, pollen, and mold, can result in inflammatory allergic reactions associated with asthma, allergic rhinitis, atopic dermatitis, and food allergies. IgE-mediated allergic reactions are initiated by the binding of the Fc domain of IgE to the high affinity IgE receptor (FcεRI) expressed on the surface of mast cells and basophils (Kinet, J. P. 1999 *Annu Rev Immunol* 17: 931-972; Gould, H. J. & Sutton, B. J. 2008 *Nat Rev Immunol* 8: 205-217). The binding of polyvalent antigens to the receptor-bound IgE leads to the release of histamines in mast cells, followed by the synthesis and release of prostaglandins, leukotrienes, and cytokines, stimulating additional inflammatory responses.

We have previously described a conformational change of IgE that has been observed by comparing the crystal structures of human IgE alone (IgE-Fc) (Wurzburg, B. A., Garman, S. C. & Jardetzky, T. S. 2000 *Immunity* 13: 375-385) to that of the IgE-Fc: FcεRI complex (Garman, S. C. et al. 2000 *Nature* 406: 259-266). The IgE heavy chain consists of the N-terminal variable domain followed by four constant domains. It is the C-terminal two constant domains (Cε3-Cε4) that mediate the high affinity binding to the receptor. The high affinity receptor is composed of three separate chains that assemble into an $\alpha\beta\gamma_2$ tetramer and it is the extracellular region of the $\alpha$-chain of FcεRI that is directly involved in binding to the IgE (Nissim, A., Jouvin, M. H. & Eshhar, Z. 1991 *Embo J* 10: 101-107; Basu, M. et al. 1993 *J Biol Chem* 268: 13118-13127; Presta, L. et al. 1994 *J Biol Chem* 269: 26368-26373; Henry, A. J. et al. 1997 *Biochemistry* 36: 15568-15578). The comparison of these structures has provided evidence that in the receptor-bound state, the IgE-Fc is in an open conformation (Wurzburg, B. A., Garman, S. C. & Jardetzky, T. S. 2000 *Immunity* 13: 375-385), whereas in the free state, the IgE-Fc can adopt a closed conformation that cannot bind receptor (Garman, S. C. et al. 2000 *Nature* 406: 259-266). Recent studies of multiple crystal forms of the IgE-Fc demonstrate a range of conformations that the Fc region can adopt, although these are all more closed as compared to the conformation in the receptor-bound state.

BRIEF SUMMARY OF THE INVENTION

A first embodiment is a polypeptide comprising an amino acid sequence that is at least 70%, 75%, 80%, 85%, 90%, or 95% identical to the amino acid sequence of a human IgE-Fc Cε3-Cε4, wherein said Cε3-Cε4 starts at amino acid 328 and ends at amino acid 547 of said IgE-Fc, using the numbering according to Donington and Bennich (1978), and wherein C 328 is an amino acid other than C and K 367 is C.

A second embodiment is a polypeptide comprising the amino acid sequence of a human IgE-Fc Cε3-Cε4, wherein said Cε3-Cε4 starts at amino acid 328 and ends at amino acid 547 of said IgE-Fc, using the numbering according to Donington and Bennich (1978), but with up to 30%, 25%, 20%, 15%, 10%, or 5% insertions, deletions, or conservative substitutions, and wherein C 328 is an amino acid other than C and K 367 is C.

A third embodiment is a polypeptide comprising the amino acid sequence of a human IgE-Fc Cε3-Cε4, wherein said Cε3-Cε4 starts at amino acid 328 and ends at amino acid 547 of said IgE-Fc, using the numbering according to Donington and Bennich (1978), and wherein C 328 is an amino acid other than C and K 367 is C.

A fourth embodiment is the polypeptide of the first, the second, or the third embodiment, wherein said polypeptide mediates high affinity binding (Kd≥~10 −8 M) to a FcεRIα.

A fifth embodiment is a polypeptide comprising the amino acid sequence of a human IgE-Fc Cε3-Cε4, wherein said Cε3-Cε4 starts at amino acid 328 and ends at amino acid 547 of said IgE-Fc, using the numbering according to Dorrington and Bennich (1978), and wherein C 328 is A and K 367 is C.

A sixth embodiment is the polypeptide of any of the first to the fifth embodiment, wherein said IgE-Fc Cε3-Cε4 sequence is labeled with a fluorophore.

A seventh embodiment is a polynucleotide comprising a nucleic acid sequence encoding the polypeptide of any of the first to the sixth embodiment.

An eighth embodiment is a polynucleotide comprising a nucleic acid sequence that hybridizes under highly stringent conditions to the complement of a naturally occurring nucleic acid sequence encoding the amino acid sequence of a human IgE-Fc Cε3-Cε4, wherein said Cε3-Cε4 starts at amino acid 328 and ends at amino acid 547 of said IgE-Fc, using the numbering according to Dorrington and Bennich (1978), and wherein C 328 is an amino acid other than C, optionally A, and K 367 is C.

A ninth embodiment is the polynucleotide of the eighth embodiment, wherein said nucleic acid sequence encodes a polypeptide that mediates high affinity binding (Kd≥~10 −8 M) to a FcεRIα.

A tenth embodiment is a polynucleotide comprising the nucleic acid sequence set forth in SEQ ID NO:1 nucleotide 10 to 669.

An eleventh embodiment is a mixture comprising the polypeptide of any of the first to the sixth embodiment in admixture with a second polypeptide comprising an amino acid sequence that is at least 70%, 75%, 80%, 85%, 90%, or 95% identical to the amino acid sequence of a human FcεRIα extracellular region, wherein said extracellular region starts at amino acid 1 and ends at amino acid 176 of said FcεRIα, using the numbering −25 to 232 according to Kochan et al. (1988).

A twelfth embodiment is a mixture comprising the polypeptide of any of the first to the sixth embodiment in admixture with a second polypeptide comprising the amino acid sequence of a human FcεRIα extracellular region, wherein said extracellular region starts at amino acid 1 and ends at amino acid 176 of said FcεRIα, using the numbering −25 to 232 according to Kochan et al. (1988), but with up to 30%, 25%, 20%, 15%, 10%, or 5% insertions, deletions, or conservative substitutions.

A thirteenth embodiment is the mixture of the eleventh or the twelfth embodiment, wherein said second polypeptide mediates high affinity binding (Kd≥~10 −8 M) to an IgE-Fc.

A fourteenth embodiment is a mixture comprising the polypeptide of any of the first to the sixth embodiment in admixture with a second polypeptide comprising the amino acid sequence of a human FcεRIα extracellular region, wherein said extracellular region starts at amino acid 1 and ends at amino acid 176 of said FcεRIα, using the numbering −25 to 232 according to Kochan et al. (1988).

A fifteenth embodiment is a method of identifying a compound that inhibits the binding of an IgE-Fc to a FcεRIα, said method comprising:

Contacting the polypeptide of any of the first to the sixth embodiment, wherein said IgE-Fc Cε3-Cε4 sequence is labeled with a fluorophore, and the second polypeptide of any of the eleventh to the fourteenth embodiment, with a test compound; and Determining whether binding of said polypeptide to said second polypeptide is decreased in the presence of said test compound (Kd of <~10 −8 M, Kd of <~10 −7 M, Kd of <~10 −6 M, Kd of <~10 −5 M, Kd of <~10 −4 M, Kd of <~10 −3 M, Kd of <~10 −2 M, or Kd of <~10 −1 M), a decrease in said binding being an indication that the test compound inhibits the binding of said polypeptide to said second polypeptide.

A sixteenth embodiment is the method of the fifteenth embodiment, wherein said decrease in binding is indicated by analysis of fluorescence polarization, FRET, or fluorescence intensity.

A seventeenth embodiment is the method of the sixteenth embodiment, wherein said decrease in binding is mediated by competitive inhibition.

An eighteenth embodiment is a process for making a compound, said process comprising carrying out the method of the fifteenth, the sixteenth, or the seventeenth embodiment, further comprising manufacturing the compound identified by said method.

A nineteenth embodiment is a product made by the process of carrying out the method of the fifteenth, the sixteenth, or the seventeenth embodiment, in some embodiments excluding IgE-Fc, MAb 15.1, and 4B11-B8.

A twentieth embodiment is the product of the nineteenth embodiment, excluding monoclonal antibodies, in some embodiments said product being a small molecule.

BRIEF DESCRIPTION OF THE DRAWINGS

FIG. 1A shows the Cys 367 mutant. FIG. 1B shows the Cys 369 mutant. FIG. 1C shows the Cys 427 mutant. FIG. 1D lists sites for fluorescent dye labeling in IgE-Fc and relative distances in the open and closed IgE-Fc conformations.

FIGS. 8A-8C show nucleotide and amino acid sequences of the wild-type and C328A/K367C mutant clones. FIG. 8A shows DNA sequences of wild-type and C328A-K367C IgE-Fc. FIG. 8B shows an alignment comparing the DNA sequences of the wild-type and C328A/K367C mutant. FIG. 8C shows amino acid sequences of the wild-type and C328A/K367C mutant IgE-Fc.

FIGS. 9A-9C show nucleotide and amino acid sequences of the light and heavy chains of the 4B11-B8 Fab. FIG. 9A shows the nucleotide and amino acid sequences of the light chain and the translation of the nucleotide sequence of the light chain. FIG. 9B shows the nucleotide and amino acid sequences of the heavy chain. FIG. 9C shows the translation of the nucleotide sequence of the heavy chain.

BRIEF DESCRIPTION OF THE SEQUENCES

Figure 1A:
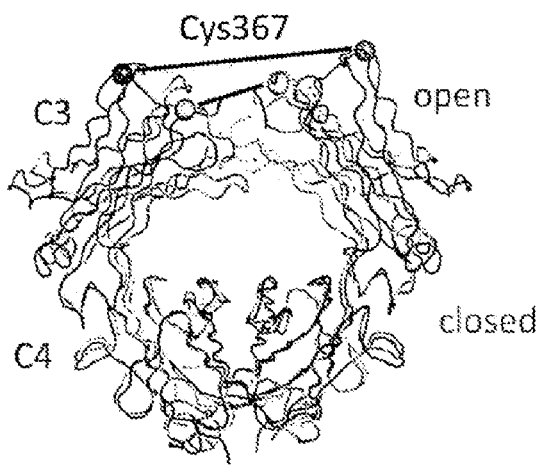
FIGS. 1A-1C show locations of residues selected for cysteine mutagenesis in the open and closed IgE-Fc conformations.

SEQ ID NO:1, referring to FIG. 8, is the nucleotide sequence of the C328A/K367C mutant clone.

SEQ ID NO:2, referring to FIG. 8, is the nucleotide sequence of the wild-type clone.

SEQ ID NO:3, referring to FIG. 8, is the amino acid sequence of the C328A/K367C mutant clone.

SEQ ID NO:4, referring to FIG. 8, is the amino acid sequence of the wild-type clone.

SEQ ID NO:5, referring to FIG. 8, is the nucleotide sequence of the "tags".

SEQ ID NO:6, referring to FIG. 8, is the amino acid sequence of the "tags".

SEQ ID NO:7, referring to FIG. 9, is the nucleotide sequence of the light chain of the 4B11-B8 FAb.

SEQ ID NO:8, referring to FIG. 9, is the amino acid sequence of the light chain of the 4B11-B8 FAb.

SEQ ID NO:9, referring to FIG. 9, is the nucleotide sequence of the heavy chain of the 4B11-B8 FAb.

SEQ ID NO:10, referring to FIG. 9, is the amino acid sequence of the heavy chain of the 4B11-B8 FAb.

DETAILED DESCRIPTION OF THE EMBODIMENTS

Unless defined otherwise, terms used herein have the same meaning as commonly understood by one of ordinary skill in the art to which this invention belongs. See, e.g., Paul Singleton and Diana Sainsbury, *Dictionary of Microbiology and Molecular Biology* (3d ed. revised, John Wiley & Sons, Chichester, England, 2006).

To efficiently identify compounds that inhibit IgE-receptor binding, we have developed a quantitative, fluorescence-based assay for detecting the binding of IgE to its receptor. We have demonstrated that this assay can be used to measure the binding of previously identified competitive inhibitors, including unlabeled IgE-Fc (Wurzburg, B. A., Garman, S. C. & Jardetzky, T. S. 2000 *Immunity* 13: 375-385), and anti-FcεRI antibody (Mab 15.1 (Mirkina, I., Schweighoffer, T. & Kricek, F. 2007 *Immunol Lett* 109: 120-128; Wang, B. et al. 1992 *J Exp Med* 175: 1353-1365)) and a novel anti-IgE antibody (4B11-B8). Mab 15.1 binds to the alpha chain of FcεRI, blocking IgE binding and reducing the release of histamine and leukotrienes from basophils (Mirkina, I., Schweighoffer, T. & Kricek, F. 2007 *Immunol Lett* 109: 120-128). 4B11-B8 is a monoclonal antibody raised against an IgE-Fc mutant that is locked in the closed conformation by a disulfide bridge and mapping experiments indicate that the IgE epitope recognized by this antibody lies outside of the receptor binding site, indicating that it may inhibit IgE binding by an allosteric mechanism. The fluorescence-binding assay can be adapted to high throughput screening for identifying inhibitors that interfere with the binding of IgE to its receptor, which is envisioned and recognized as leading to new anti-allergy drugs.

DEFINITIONS

The term "FcεRIα extracellular region" or the like refers to an extracellular domain of a FcεRIα protein that is the portion of the FcεRIα chain that is exposed to the environment outside the cell and that binds to an IgE-Fc. For the nucleotide and amino acid sequence of a human IgE-Fc, see Flanagan, J. G. and Rabbitts, T. H. 1982 *EMBO J.* 1:655-660. The term "FcεRIα extracellular region" or the like refers also to a polypeptide (preferably of mammalian origin, e.g., human) or, as context requires, a polynucleotide encoding such a polypeptide, that is capable of interacting with an IgE-Fc (preferably of mammalian origin, e.g., human) and has at least one of the following features: (1) an amino acid sequence of a naturally occurring mammalian FcεRIα extracellular region or a fragment thereof, e.g., an amino acid sequence that starts at amino acid 1 and ends at amino acid 176 of a human FcεRIα, using the numbering −25 to 232, and representative sequence, according to Kochan, J. et al. 1988 *Nucleic Acids Res.* 16:3584-3584, or a fragment thereof; (2) an amino acid sequence substantially identical to, e.g., at least 70%, 75%, 80%, 85%, 90%, 95%, 98%, or 99% identical to, an amino acid sequence that starts at amino acid 1 and ends at amino acid 176 of a human FcεRIα, using the numbering −25 to 232, and representative sequence, according to Kochan, J. et al. 1988 *Nucleic Acids Res.* 16:3584-3584, or a fragment thereof; (3) an amino acid sequence that is encoded by a naturally occurring mammalian FcεRIα extracellular region nucleotide sequence or a fragment thereof, e.g., a nucleotide sequence that encodes an amino acid sequence that starts at amino acid 1 and ends at amino acid 176 of a human FcεRIα, using the numbering −25 to 232, and representative sequence, according to Kochan, J. et al. 1988 *Nucleic Acids Res.* 16:3584-3584, or a fragment thereof, a naturally occurring nucleotide sequence being represented according to Kochan, J. et al. 1988 *Nucleic Acids Res.* 16:3584-3584; (4) an amino acid sequence encoded by a nucleotide sequence degenerate to a naturally occurring mammalian FcεRIα extracellular region nucleotide sequence or a fragment thereof, e.g., a nucleotide sequence that encodes an amino acid sequence that starts at amino acid 1 and ends at amino acid 176 of a human FcεRIα, using the numbering −25 to 232, and representative sequence, according to Kochan, J. et al. 1988 *Nucleic Acids Res.* 16:3584-3584, or a fragment thereof, a naturally occurring nucleotide sequence being represented according to Kochan, J. et al. 1988 *Nucleic Acids Res.* 16:3584-3584; or (5) an amino acid sequence encoded by a nucleotide sequence that hybridizes under stringent conditions, e.g., highly stringent conditions, to a naturally occurring mammalian FcεRIα extracellular region nucleotide sequence or a fragment thereof, e.g., a nucleotide sequence that encodes an amino acid sequence that starts at amino acid 1 and ends at amino acid 176 of a human FcεRIα, using the numbering −25 to 232, and representative sequence, according to Kochan, J. et al. 1988 *Nucleic Acids Res.* 16:3584-3584, or a fragment thereof, a naturally occurring nucleotide sequence being represented according to Kochan, J. et al. 1988 *Nucleic Acids Res.* 16:3584-3584. In addition, other nonhuman and nonmammalian FcεRIα extracellular regions are contemplated as useful in the disclosed methods.

The term "IgE-Fc Cε3-Cε4" or the like refers to a third and fourth C-terminal constant domain, Cε3 and Cε4, of an IgE heavy chain that mediates binding to a FcεRIα. For the nucleotide and amino acid sequence of a human FcεRIα, see Kochan, J. et al. 1988 *Nucleic Acids Res.* 16:3584-3584. The term "IgE-Fc Cε3-Cε4" or the like refers also to a polypeptide (preferably of mammalian origin, e.g., human) or, as context requires, a polynucleotide encoding such a polypeptide, that is capable of interacting with a FcεRIα (preferably of mammalian origin, e.g., human) and has at least one of the following features: (1) an amino acid sequence of a naturally occurring mammalian IgE-Fc Cε3-Cε4 or a fragment thereof, e.g., an amino acid sequence that starts at amino acid 328 and ends at amino acid 547 of a human IgE-Fc, using the numbering according to Dorrington, K. J. and Bennich, H. H. 1978 *Immunol. Rev.* 41:3-25, and representative sequence according to Flanagan, J. G. and Rabbitts, T. H. 1982 *EMBO J.* 1:655-660, as exemplified by Wurzburg, B. A., Garman, S. C. & Jardetzky, T. S. 2000 *Immunity* 13: 375-385, or a fragment thereof; (2) an amino acid sequence substantially identical to, e.g., at least 70%, 75%, 80%, 85%, 90%, 95%, 98%, or 99% identical to, an amino acid sequence that starts at amino acid 328 and ends at amino acid 547 of a human IgE-Fc, using the numbering according to Donington, K. J. and Bennich, H. H. 1978 Immunol. Rev. 41:3-25, and representative sequence according to Flanagan, J. G. and Rabbitts, T. H. 1982 *EMBO J.* 1:655-660, as exemplified by Wurzburg, B. A., Garman, S. C. & Jardetzky, T. S. 2000 *Immunity* 13: 375-385, or a fragment thereof; (3) an amino acid sequence that is encoded by a naturally occurring mammalian IgE-Fc Cε3-Cε4 nucleotide sequence or a fragment thereof, e.g., a nucleotide sequence that encodes an amino acid sequence that starts at amino acid 328 and ends at amino acid 547 of a human IgE-Fc, using the numbering according to Dorrington, K. J. and Bennich, H. H. 1978 *Immunol. Rev.* 41:3-25, and representative sequence according to Flanagan, J. G. and Rabbitts, T. H. 1982 *EMBO J.* 1:655-660, as exemplified by Wurzburg, B. A., Garman, S.

C. & Jardetzky, T. S. 2000 *Immunity* 13: 375-385, or a fragment thereof, a naturally occurring nucleotide sequence being represented according to Flanagan, J. G. and Rabbitts, T. H. 1982 *EMBO J.* 1:655-660; (4) an amino acid sequence encoded by a nucleotide sequence degenerate to a naturally occurring mammalian IgE-Fc Cϵ3-Cϵ4 nucleotide sequence or a fragment thereof, e.g., a nucleotide sequence that encodes an amino acid sequence that starts at amino acid 328 and ends at amino acid 547 of a human IgE-Fc, using the numbering according to Dorrington, K. J. and Bennich, H. H. 1978 *Immunol. Rev.* 41:3-25, and representative sequence according to Flanagan, J. G. and Rabbitts, T. H. 1982 *EMBO J.* 1:655-660, as exemplified by Wurzburg, B. A., Garman, S. C. & Jardetzky, T. S. 2000 *Immunity* 13: 375-385, or a fragment thereof, a naturally occurring nucleotide sequence being represented according to Flanagan, J. G. and Rabbitts, T. H. 1982 *EMBO J.* 1:655-660; or (5) an amino acid sequence encoded by a nucleotide sequence that hybridizes under stringent conditions, e.g., highly stringent conditions, to a naturally occurring mammalian IgE-Fc Cϵ3-Cϵ4 nucleotide sequence or a fragment thereof, e.g., a nucleotide sequence that encodes an amino acid sequence that starts at amino acid 328 and ends at amino acid 547 of a human IgE-Fc, using the numbering according to Dorrington, K. J. and Bennich, H. H. 1978 *Immunol. Rev.* 41:3-25, and representative sequence according to Flanagan, J. G. and Rabbitts, T. H. 1982 *EMBO J.* 1:655-660, as exemplified by Wurzburg, B. A., Garman, S. C. & Jardetzky, T. S. 2000 *Immunity* 13: 375-385, or a fragment thereof, a naturally occurring nucleotide sequence being represented according to Flanagan, J. G. and Rabbitts, T. H. 1982 *EMBO J.* 1:655-660. In addition, other nonhuman and nonmammalian IgE-Fc Cϵ3-Cϵ4 domains are contemplated as useful in the disclosed methods.

Alignment means the process of lining up two or more sequences to achieve maximal levels of identity (and conservation, in the case of amino acid sequences) for the purpose of assessing the degree of similarity and the possibility of homology. Algorithm means a fixed procedure embodied in a computer program. Bit score means the value S' is derived from the raw alignment score S in which the statistical properties of the scoring system used have been taken into account. BLAST means Basic Local Alignment Search Tool (Altschul S. F. et al. 1990 *J Mol Biol.* 215: 403-410), that is, a sequence comparison algorithm optimized for speed used to search sequence databases for optimal local alignments to a query. The initial search is done for a word of length "W" that scores at least "T" when compared to the query using a substitution matrix. Word hits are then extended in either direction in an attempt to generate an alignment with a score exceeding the threshold of "S". The "T" parameter dictates the speed and sensitivity of the search. A tool for aligning two sequences provided by the user exploits the BLAST algorithm to align sequences as if they were found in a database search. Generally speaking, one requires a 30% identity in sequence to consider that two polypeptides match. BLOSUM means Blocks Substitution Matrix, which is a substitution matrix in which scores for each position are derived from observations of the frequencies of substitutions in blocks of local alignments in related proteins. Conservation means changes at a specific position of an amino acid or (less commonly, DNA) sequence that preserve the physico-chemical properties of the original residue. Domain means a discrete portion of a protein assumed to fold independently of the rest of the protein and possessing its own function. DUST means a program for filtering low complexity regions from nucleic acid sequences. E value means expectation value, which is the number of different alignments with scores equivalent to or better than S that are expected to occur in a database search by chance. The lower the E value, the more significant the score. FASTA means the first widely used algorithm for database similarity searching. The program looks for optimal local alignments by scanning the sequence for small matches called "words". Initially, the scores of segments in which there are multiple word hits are calculated ("init1"). Later the scores of several segments may be summed to generate an "initn" score. An optimized alignment that includes gaps is shown in the output as "opt". The sensitivity and speed of the search are inversely related and controlled by the "k-tup" variable which specifies the size of a "word".

A gap means a space introduced into an alignment to compensate for insertions and deletions in one sequence relative to another. To prevent the accumulation of too many gaps in an alignment, introduction of a gap causes the deduction of a fixed amount (the gap score) from the alignment score. Extension of the gap to encompass additional nucleotides or amino acid is also penalized in the scoring of an alignment. Global alignment means the alignment of two nucleic acid or protein sequences over their entire length. H means the relative entropy of the target and background residue frequencies. It can be thought of as a measure of the average information (in bits) available per position that distinguishes an alignment from chance. At high values of H, short alignments can be distinguished by chance, whereas at lower H values, a longer alignment may be necessary. Homology means similarity attributed to descent from a common ancestor. HSP means high-scoring segment pair, e.g., local alignments with no gaps that achieve one of the top alignment scores in a given search. Identity means the extent to which two (nucleotide or amino acid) sequences are invariant. K means a statistical parameter used in calculating BLAST scores that can be thought of as a natural scale for search space size. The value K is used in converting a raw score (S) to a bit score (S'). Lambda means a statistical parameter used in calculating BLAST scores that can be thought of as a natural scale for scoring system. The value lambda is used in converting a raw score (S) to a bit score (S'). Local alignment means the alignment of some portion of two nucleic acid or protein sequences. Low Complexity Region (LCR) means regions of biased composition including homopolymeric runs, short-period repeats, and more subtle overrepresentation of one or a few residues. The SEG program is used to mask or filter LCRs in amino acid queries. The DUST program is used to mask or filter LCRs in nucleic acid queries. Motif means a short conserved region in a protein sequence. Motifs are frequently highly conserved parts of domains. Multiple sequence alignment means an alignment of three or more sequences with gaps inserted in the sequences such that residues with common structural positions and/or ancestral residues are aligned in the same column. Clustal W is one of the most widely used multiple sequence alignment programs. Optimal alignment means an alignment of two sequences with the highest possible score. P value means the probability of an alignment occurring with the score in question or better. The p value is calculated by relating the observed alignment score, S, to the expected distribution of HSP scores from comparisons of random sequences of the same length and composition as the query to the database. The most highly significant P values will be those close to 0. P values and E values are different ways of representing the significance of the alignment.

PAM means percent accepted mutation, which is a unit to quantify the amount of evolutionary change in a protein sequence. 1.0 PAM unit, is the amount of evolution which will change, on average, 1% of amino acids in a protein sequence. A PAM(x) substitution matrix is a look-up table in which scores for each amino acid substitution have been calculated based on the frequency of that substitution in closely related proteins that have experienced a certain amount (x) of evolutionary divergence. Profile means a table that lists the frequencies of each amino acid in each position of protein sequence. Frequencies are calculated from multiple alignments of sequences containing a domain of interest. PSSM means position-specific scoring matrix, which gives the log-odds score for finding a particular matching amino acid in a target sequence. Query means the input sequence (or other type of search term) with which all of the entries in a database are to be compared. Raw Score means the score of an alignment, S, calculated as the sum of substitution and gap scores. Substitution scores are given by a look-up table. Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15) and a low value for L (1-2). Similarity means the extent to which nucleotide or protein sequences are related. The extent of similarity between two sequences can be based on percent sequence identity and/or conservation. In BLAST similarity refers to a positive matrix score. SEG means a program for filtering low complexity regions in amino acid sequences. Residues that have been masked are represented as "X" in an alignment. SEG filtering is performed by default in the blastp subroutine of BLAST 2.0. Substitution means the presence of a non-identical amino acid at a given position in an alignment. If the aligned residues have similar physico-chemical properties the substitution is said to be "conservative". Substitution matrix means a scoring system containing values proportional to the probability that amino acid i mutates into amino acid j for all pairs of amino acids. Such matrices are constructed by assembling a large and diverse sample of verified pairwise alignments of amino acids. If the sample is large enough to be statistically significant, the resulting matrices should reflect the true probabilities of mutations occurring through a period of evolution. Unitary matrix means a scoring system in which only identical characters receive a positive score.

The common amino acids are grouped according to whether their side chains are acidic, basic, uncharged polar, or nonpolar. The side chains determine their physico-chemical properties. Of the 20 amino acids found in proteins, there are equal numbers of polar and non-polar side chains. However, some side chains considered polar are large enough to have some non-polar properties, e.g., Tyr, Thr, Arg, and Lys.

| Amino acid | 3 letter name | 1 letter name | Side chain |
| --- | --- | --- | --- |
| Aspartic acid | Asp | D | Negative (polar) |
| Glutamic acid | Glu | E | Negative (polar) |
| Arginine | Arg | R | Positive (polar) |
| Lysine | Lys | K | Positive (polar) |
| Histidine | His | H | Positive (polar) |
| Asparagine | Asn | N | Uncharged polar |
| Glutamine | Gln | Q | Uncharged polar |
| Serine | Ser | S | Uncharged polar |
| Threonine | Thr | T | Uncharged polar |
| Tyrosine | Tyr | Y | Uncharged polar |
| Alanine | Ala | A | Nonpolar |
| Glycine | Gly | G | Nonpolar |
| Valine | Val | V | Nonpolar |
| Leucine | Leu | L | Nonpolar |
| Isoleucine | Ile | I | Nonpolar |
| Proline | Pro | P | Nonpolar |
| Phenylalanine | Phe | F | Nonpolar |
| Methionine | Met | M | Nonpolar |
| Tryptophan | Trp | W | Nonpolar |
| Cysteine | Cys | C | Nonpolar |

Hybridization means the process whereby two complementary nucleic acid strands form a base-paired duplex molecule. Single stranded nucleic acids hydrogen bond to each other efficiently, following Watson-Crick base pairing rules, at approximately 20-25 degrees centigrade below their melting point. To say it a different way, when hybridizing a probe to the DNA or RNA on a membrane, we adjust the solution conditions (for example, the salt concentration) so that the melting point of the nucleic acids is approximately 20-25 degrees higher than the incubation temperature. Lowering the salt concentration lowers the melting point, as does the addition of formamide. A typical condition for high stringency hybridization is: 6×SSC, 0.2% SDS, 1×Denhardt's blocking solution, or 1% w/v milk, 10-50 ng/ml probe (denatured), 65° C. incubation, with agitation, for 18-24 hours. Following a period of hybridization, it is necessary to wash off the probe that is loosely bound to the membrane (i.e., nonspecifically bound). This is typically done under high stringency conditions by washing the filter several times at 65° C. in decreasing salt concentrations (i.e., 3×SSC/0.2% SDS, then 1×SSC/0.2% SDS).

What are small molecules? We best know what they are not—Nature's DNA, RNA and protein macromolecules residing within their cellular contexts. Cells make small molecules—naturally occurring small molecules—but chemical biologists in the laboratory using, for example, DNA template-mediated, and target- and diversity-oriented organic synthesis, peptide and carbohydrate synthesis, and enzyme-mediated synthesis, also make them. Chemical biologists make both small and large "small molecules". They make them in tubes and cells, on glass surfaces, in monolayers, and even on phage viruses.

MANIPULATING PROTEINS, DNA, AND RNA

According to the central dogma of molecular biology, DNA is transcribed into RNA, and RNA is translated into protein; one gene makes one protein. Genes can be cloned using DNA libraries. Any DNA fragment can be cloned. In molecular biology, the term DNA cloning is used in two senses. In one sense, it literally refers to the act of making many identical copies of a DNA molecule—the amplification of a particular DNA sequence. However, the term also describes the isolation of a particular stretch of DNA (often a particular gene) from the rest of a cell's DNA, because this isolation is greatly facilitated by making many identical copies of the DNA of interest. In both cases, cloning refers to the act of making many genetically identical copies.

DNA cloning in its most general sense can be accomplished in several ways. The simplest involves inserting a particular fragment of DNA into the purified DNA genome of a self-replicating genetic element—generally a virus or a plasmid. A DNA fragment containing a human gene, for example, can be joined in a test tube to the chromosome of a bacterial virus, and the new recombinant DNA molecule can then be introduced into a bacterial cell, where the inserted DNA fragment will be replicated along with the DNA of the virus. Starting with only one such recombinant DNA molecule that infects a single cell, the normal replication mechanisms of the virus can produce more than 10 to the power of 12 identical virus DNA molecules in a single day, thereby amplifying the amount of the inserted human DNA fragment by the same factor. A virus or plasmid used in this way is known as a cloning vector, and the DNA propagated by insertion into it is said to have been cloned.

To isolate a specific gene, one begins by constructing a DNA library—a comprehensive collection of cloned DNA fragments from a cell, tissue, or organism. This library includes, one hopes, at least one fragment that contains the gene of interest. Libraries can be constructed with either a virus or a plasmid vector and are generally housed in a population of bacterial cells. The principles underlying the methods used for cloning genes are the same for either type of cloning vector, although the details may differ. Today, most cloning is performed with plasmid vectors.

The plasmid vectors most widely used for gene cloning are small circular molecules of double-stranded DNA derived from larger plasmids that occur naturally in bacterial cells. They generally account for only a minor fraction of the total host bacterial cell DNA, but they can easily be separated owing to their small size from chromosomal DNA molecules, which are large and precipitate as a pellet upon centrifugation. For use as cloning vectors, the purified plasmid DNA circles are first cut with a restriction nuclease to create linear DNA molecules. The genomic DNA to be used in constructing the library is cut with the same restriction nuclease, and the resulting restriction fragments (including those containing the gene to be cloned) are then added to the cut plasmids and annealed via their cohesive ends to form recombinant DNA circles. These recombinant molecules containing foreign DNA inserts are then covalently sealed with the enzyme DNA ligase.

In the next step in preparing the library, the recombinant DNA circles are introduced into bacterial cells that have been made transiently permeable to DNA. These bacterial cells are now said to be transfected with the plasmids. As the cells grow and divide, doubling in number every 30 minutes, the recombinant plasmids also replicate to produce an enormous number of copies of DNA circles containing the foreign DNA. Many bacterial plasmids carry genes for antibiotic resistance, a property that can be exploited to select those cells that have been successfully transfected; if the bacteria are grown in the presence of the antibiotic, only cells containing plasmids will survive. Each original bacterial cell that was initially transfected contains, in general, a different foreign DNA insert; this insert is inherited by all of the progeny cells of that bacterium, which together form a small colony in a culture dish.

Two types of DNA libraries serve different purposes. Cleaving the entire genome of a cell with a specific restriction nuclease and cloning each fragment as just described produces a very large number of DNA fragments—on the order of a million for a mammalian genome. The fragments are distributed among millions of different colonies of transfected bacterial cells. Each of the colonies is composed of a clone of cells derived from a single ancestor cell, and therefore harbors many copies of a particular stretch of the fragmented genome. Such a plasmid is said to contain a genomic DNA clone, and the entire collection of plasmids is called a genomic DNA library. But because the genomic DNA is cut into fragments at random, only some fragments contain genes. Many of the genomic DNA clones obtained from the DNA of a higher eukaryotic cell contain only noncoding DNA, which makes up most of the DNA in such genomes.

An alternative strategy is to begin the cloning process by selecting only those DNA sequences that are transcribed into mRNA and thus are presumed to correspond to protein-encoding genes. This is done by extracting the mRNA from cells and then making a DNA copy of each mRNA molecule present—a so-called complementary DNA, or cDNA. The copying reaction is catalyzed by the reverse transcriptase enzyme of retroviruses, which synthesizes a complementary DNA chain on an RNA template. The single-stranded cDNA molecules synthesized by the reverse transcriptase are converted into double-stranded cDNA molecules by DNA polymerase, and these molecules are inserted into a plasmid or virus vector and cloned. Each clone obtained in this way is called a cDNA clone, and the entire collection of clones derived from one mRNA preparation constitutes a cDNA library.

There are some important differences between genomic DNA clones and cDNA clones. Genomic clones represent a random sample of all the DNA sequences in an organism and, with very rare exceptions, are the same regardless of the cell type used to prepare them. By contrast, cDNA clones contain only those regions of the genome that have been transcribed into mRNA. Because the cells of different tissue types produce distinct sets of mRNA molecules, a distinct cDNA library is obtained for each type of cell used to prepare the library.

The most important advantage of cDNA clones is that they contain the uninterrupted coding sequence of a gene. Eukaryotic genes usually consist of short coding sequences of DNA (exons) separated by much longer noncoding sequences (introns); the production of mRNA entails the removal of the noncoding sequences from the initial RNA transcript and the splicing together of the coding sequences. Bacterial cells will not make these modifications to the RNA produced from a gene of a higher eukaryotic cell. Thus, when the aim of the cloning is either to deduce the amino acid sequence of the protein from the DNA sequence or to produce the protein in bulk by expressing the cloned gene in a bacterial cell, it is much preferable to start with cDNA. cDNA libraries have the additional advantage of representing alternatively spliced mRNAs produced from a given cell or tissue.

Genes can be selectively amplified by PCR. Now that so many genome sequences are available, among investigators, and from commercial sources, genes can be cloned directly without the need to first construct DNA libraries. A technique called polymerase chain reaction (PCR) makes this rapid cloning possible. Starting with an entire genome, PCR allows the DNA from a selected region to be amplified several billionfold, effectively "purifying" this DNA away from the remainder of the genome.

To begin, a pair of DNA oligonucleotides, chosen to flank the desired nucleotide sequence of the gene, are synthesized by chemical methods. These oligonucleotides are then used to prime DNA synthesis on single strands generated by heating the DNA from the entire genome. The newly synthesized DNA is produced in a reaction catalyzed in vitro by a purified DNA polymerase, and the primers remain at the 5' ends of the final DNA fragments that are made.

Nothing special is produced in the first cycle of DNA synthesis; the power of the PCR method is revealed only after repeated rounds of DNA synthesis. Every cycle doubles the amount of DNA synthesized in the previous cycle. Because each cycle requires a brief heat treatment to separate the two strands of the template DNA double helix, the technique requires the use of a special DNA polymerase, isolated from a thermophilic bacterium, that is stable at much higher temperatures than normal so that it is not denatured by the repeated heat treatments. With each round of DNA synthesis, the newly generated fragments serve as templates in their turn, and within a few cycles the predominant product is a single species of DNA fragment whose length corresponds to the distance between the two original primers.

In practice, effective DNA amplification requires 2-30 reaction cycles, with the products of each cycle serving as the DNA templates for the next—hence the term polymerase "chain reaction." A single cycle requires only about 5 minutes, and the entire procedure can be easily automated. PCR thereby makes possible the "cell-free molecular cloning" of a DNA fragment in a few hours, compared with the several days for standard cloning procedures. This technique is now used routinely to clone DNA from genes of interest directly—starting either from genomic DNA or from mRNA isolated from cells.

Cells can be used as factories to produce specific proteins. The vast majority of the thousands of different proteins in a cell, including many with crucially important functions, are present in very small amounts. In the past, for most of them, it has been extremely difficult, if not impossible, to obtain more than a few micrograms of pure material. One of the most important contributions of DNA cloning and genetic engineering to cell biology is that they have made it possible to produce any of the cell's proteins in a nearly unlimited amount.

Large amounts of the desired protein are produced in living cells by using expression vectors. These are generally plasmids that have been designed to produce a large amount of a stable mRNA that can be efficiently translated into protein in the transfected bacterial, yeast, insect, or mammalian cell. A plasmid vector is engineered to contain a highly active promoter, which causes unusually large amounts of mRNA to be produced from an adjacent protein-coding gene inserted into the plasmid vector. Depending on the characteristics of the cloning vector, the plasmid is introduced into bacterial, yeast, insect, or mammalian cells, where the inserted gene is efficiently transcribed and translated into protein. To prevent the high level of the foreign protein from interfering with the transfected cells' growth, the expression vector is often designed to delay the synthesis of the foreign mRNA and protein until shortly before the cells are harvested and lysed.

Because the desired protein made from an expression vector is produced inside a cell, it must be purified away from the host-cell proteins after cell lysis; but because it is a plentiful species in the cell lysate (often 1-10% of the total cell protein), the purification is usually easy to accomplish in only a few steps. In order to purify a protein, it first must be extracted from inside the cell, unless it is secreted into the medium. The cells are typically homogenized to produce a homogenate or slurry. The homogenate is typically fractionated into different components by centrifugation. After centrifugation, proteins are often separated by chromatography. Secreted, soluble proteins are isolated from the supernatants of infected cells after pelleting the cells by centrifugation and do not require cell lysis. Many expression vectors have been designed to add a molecular tag—a cluster of histidine residues or a small marker protein—to the expressed protein to allow easy purification by affinity chromatography. A variety of expression vectors are available, each engineered to function in the type of cell in which the protein is to be made.

Chemical reactions have been devised to synthesize directly specific sequences of nucleic acids or amino acids. These methodologies provide direct sources of biological molecules and do not rely on any cells or enzymes. Chemical synthesis is the method of choice for obtaining nucleic acids in the range of 100 nucleotides or fewer, which, under the basic concept of de novo gene synthesis, may be assembled into larger constructs using some form of polymerase chain assembly or ligase chain reaction approach. Chemical synthesis is also routinely used to produce specific peptides that, when chemically coupled to other proteins, are used to generate antibodies against the peptide.

DNA can be rapidly sequenced. Nucleotide sequences are used to predict the amino acid sequences of proteins. Genes that encode proteins are demarcated by open reading frames that begin with an initiation codon, usually ATG, and end with a termination codon.

Site-directed mutagenesis makes use of a synthetic oligonucleotide to modify the protein-coding region of a gene. A recombinant plasmid containing the gene of interest is separated into its two DNA strands. A synthetic oligonucleotide primer corresponding to part of the gene sequence but containing a single altered nucleotide at a predetermined point is added to the single-stranded DNA under conditions that permit imperfect DNA hybridization. The primer hybridizes to the DNA, forming a single mismatched nucleotide pair. The recombinant plasmid is made double-stranded by in vitro DNA synthesis, starting from the primer, followed by sealing with DNA ligase. The double-stranded DNA is introduced into a cell, where it is replicated. Replication using one strand of the template produces a normal DNA molecule, but replication using the other strand, the one that contains the primer, produces a DNA molecule carrying the desired mutation. Only half of the progeny cells will end up with a plasmid that contains the desired mutant gene. However, a progeny cell that contains the mutated gene can be identified, separated from other cells, and cultured to produce a pure population of cells, all of which carry the mutated gene. With an oligonucleotide of the appropriate sequence, more than one amino acid substitution can be made at a time, or one or more amino acids can be inserted or deleted. It is also standard to create site-directed mutation by using the appropriate oligonucleotides and PCR, instead of plasmid replication, to amplify the mutated gene.

The monoclonal antibody procedure requires hybrid cell technology, and it involves propagating a clone of cells from a single antibody-secreting B lymphocyte to obtain a homogeneous preparation of antibodies in large quantities. B lymphocytes normally have a limited life-span in culture, but individual antibody-producing B lymphocytes from an immunized mouse or rat, when fused with cells derived from a transformed B lymphocyte cell line, can give rise to hybrids that have both the ability to make a particular antibody and the ability to multiply indefinitely in culture. These hybridomas are propagated as individual clones, each of which provides a permanent and stable source of a single type of monoclonal antibody. Each type of monoclonal antibody recognizes a single type of antigenic site.

MODULATION OF PROTEIN-PROTEIN INTERACTIONS WITH SMALL MOLECULES

The principal feasibility of using small organic molecules to target protein-protein interactions has been demonstrated. Even though these studies demonstrate the general feasibility of modulating protein-protein interactions with small organic molecules, the application of this principle to drug discovery research has posed a number of problems. The first difficulty arises over the identification of lead compounds to target protein-protein interactions for which no naturally occurring protein-binding small molecules are known. However, if the protein-protein interface consists of short continuous binding domains, peptidic binding-site mimics lend themselves as lead compounds for subsequent optimization. The existence of short continuous sequence motifs mediating the protein-protein interactions between integrins and their extracellular ligands has aided in the discovery of numerous small-molecule inhibitors to date. However, many protein-protein interfaces consist of noncontinuous binding epitopes in the primary protein sequence, which makes it difficult to rationally design binding-site mimics Secondly, a recent study revealed that the area of the recognition sites in protein-protein complexes is usually greater than 1100 Å$^2$, with the exact area depending on the nature of the complex, which vastly exceeds the potential binding area of a low-molecular-weight compound. Attempting to modulate such protein-protein interactions with low-molecular-weight compounds which satisfy the requirements for orally deliverable drugs appear to be unfeasible at first glance. However, it has been demonstrated that a minor fraction of the protein-protein interface residues can in fact account for the majority of the free energy of binding between proteins. Such hot spots of binding free energy appear to be common in protein-protein interfaces. Hot-spot amino acid residues tend to be clustered together at the center of a protein-protein interface and are surrounded by energetically less important amino acid residues that probably serve to occlude bulk solvent. The third difficulty is that protein-protein interfaces are often flat and may therefore lack binding sites for small molecules. Despite these difficulties, a number of small organic modulators of large protein-protein interactions have been identified to date.

Herein, several pharmaceutically interesting protein-protein interactions which, for the most part, involve large, possibly discontinuous binding sites are discussed, and will familiarize the reader with the strategies employed for the identification of small molecule modulators (inhibitors as well as inducers and stabilizers) of these protein-protein interactions. The approach involves the in vitro or cell-based screening of chemical libraries for modulators of protein-protein interactions. Further advances in assay development and screening technologies will allow even more rapid high-throughput screening of chemical libraries.

Inhibitors of the Interaction between Bcl-xL or Bcl-2 and Bak-BH3 Domains. Drug resistance is a serious problem in cancer chemotherapy. Most conventional chemotherapeutic agents damage cellular components, and this can result in a variety of post-damage responses. One of the desired effects is the induction of apoptosis, a highly regulated program of cellular suicide which plays an important role in the body's defense against cells that threaten to escape normal proliferation control mechanisms. Overexpression of the anti-apoptotic bcl-2 family genes bcl-2 and bcl-xL has frequently been observed in several solid human tumors, and has been linked to resistance of the tumors to chemotherapy. Bcl-2 was furthermore validated as a tumor target by the effects of an antisense oligonucleotide (Genasense, Genta Inc., USA) which was to be tested in clinical trials in combination with cytotoxic chemotherapy for the treatment of various cancers. Bcl-2 and Bcl-xL are assumed to prevent apoptosis by inhibiting the function of other, pro-apoptotic members of the Bcl-2 family, such as Bax and Bak, by binding to their BH3 (Bcl-2-homology 3) domain. Small-molecule inhibitors of the interactions between Bcl-2 or Bcl-xL and the BH3 domain of pro-apoptotic Bcl-2 family proteins are therefore anticipated to restore the biological functions of pro-apoptotic Bcl-2 family members, and could possibly render drug susceptibility to cancers which are resistant to chemotherapy because of overexpression of anti-apoptotic Bcl-2 family genes.

To identify small-molecule inhibitors of the interaction between Bcl-xL and the BH3 domain of Bak, investigators set up an in vitro assay based on fluorescence polarization (FP). This homogeneous assay is generally applicable for the analysis of protein-protein interactions if the molecular weight of the larger protein is considerably higher than the weight of the smaller protein or peptide, and can easily be adapted to a high-throughput format. The degree of interaction between the fluorescent-labeled BH3 domain of Bak and recombinant Bcl-xL protein was assessed by analyzing the polarization of the emitted fluorescence upon excitation with polarized light. In the absence of an inhibitor compound, the small fluorescent-labeled BH3 peptide is bound to the larger Bcl-xL protein. Since the spatial orientation of the large peptide/protein complex hardly changes between the time of fluorescence excitation and fluorescence emission, the polarization of the emitted fluorescence is relatively high Inhibitors of Bcl-xL/Bak-BH3 interactions liberate the small fluorescent-labeled BH3 peptide and are detected because of the increased rotational mobility of this peptide in the unbound state which leads to a reduction of the fluorescence polarization.

A commercially available library consisting of 16320 chemicals was screened, and three compounds termed BH3I-1, BH3I-1', and BH3I-2, were identified as inhibitors of the Bcl-xL/Bak-BH3 interaction (Ki=2.4-4.1 µM). Closely related analogues were also found to be Bcl-xL/Bak-BH3 inhibitors. NMR spectroscopy experiments demonstrated that the inhibitor compounds target the BH3-binding pocket of Bcl-xL. The Bcl-xL/Bak-BH3 inhibitors restored the function of the pro-apoptotic Bcl-2 family members in cell culture, and allowed previously resistant cells to undergo apoptosis. Using an unrelated approach, investigators reported that a mixture of antimycin A isomers, previously used as an inhibitor of mitochondrial electron transfer, is also a competitive inhibitor of the binding of the BH3-domain of Bcl-2 or Bcl-xL to a BH3 peptide. The chemical optimization of these inhibitors could lead to novel approaches in the treatment of cancers resistant to chemotherapy.

Inhibitors of Myc/Max Dimerization. The transcription factor c-Myc is estimated to be involved in one out of seven human cancer deaths. In Burkitt's lymphoma and other lymphoid malignancies, the c-myc gene is translocated into the vicinity of an immunoglobulin enhancer, which results in constitutive overexpression. The c-myc gene is also amplified in lung and breast carcinomas, and elevated expression of the c-Myc protein is found in the majority of colon carcinomas. Targeted overexpression of c-myc causes hematopoetic tumors in transgenic mice, and sustained activation of c-Myc is sufficient to induce premalignant changes in the skin epidermis. Since the oncogenic activity of c-Myc entirely depends on binding to its activation partner Max, inhibitors of c-Myc/Max interactions have the potential to regulate c-Myc activity and be of pharmacological interest for the treatment of cancers that depend on sustained activation of c-Myc.

c-Myc and Max belong to the basic helix-loop-helix leucine zipper (bHLH-LZ) protein family. From the crystal structure of the related Max/Max homodimer, it is to be assumed that the Myc/Max dimer forms a parallel, left-handed, four-helix bundle, with each monomer containing two a-helical segments separated by a loop. While the basic region and the N-terminal helices mediate binding to specific DNA sequences in the promoters of c-Myc target genes, the dimerization interface consists of the C-terminal helix motif and the leucine zipper, which forms a parallel, two stranded α-helical coiled coil. The protein-protein interface is formed by mostly hydrophobic, buried, amino acid residues.

As a result of the parallel alignment and the identical length of the dimerization motifs of c-Myc and Max, a binding assay based on fluorescence resonance energy transfer (FRET) is ideally suited to screen for inhibitors of the Myc/Max interaction. FRET can occur between two fluorophores if the emission spectrum of the donor fluorophore overlaps with the absorption spectrum of the acceptor fluorophore. As the efficiency of FRET is dependent on the inverse sixth power of the distance between the fluorophores, this method allows the analysis of binding equilibria between molecules fused to two suitable fluorophores. Investigators expressed the dimerization domains of c-Myc and Max as fusion proteins with cyan fluorescent protein (CFP) and yellow fluorescent protein (YFP), respectively. Upon excitation of CFP, the close proximity between the fluorophores in the c-Myc/Max dimer allowed for energy transfer from CFP to YFP. Inhibitors of c-Myc/Max dimerization-domain interactions increased the average distance between the c-Myc and Max polypeptides and thereby decreased the amount of energy transferred between the fluorophores, which led to characteristic changes in the fluorescence spectrum.

Screening of chemical libraries encompassing approximately 7000 compounds resulted in the discovery of four small-molecule antagonists of c-Myc/Max dimerization-domain interactions which were subsequently validated in independent in vitro assays. The two most active inhibitors in vitro, IIA4B20 and IIA6B17, also inhibited c-Myc-induced oncogenic transformation of chicken embryo fibroblasts with IC50 values of approximately 20 µM. Improved inhibitors of c-Myc/Max interactions which may emerge from secondary libraries could not only serve as lead structures for drug development, but might also be useful as molecular tools to aid in the identification of downstream target genes of c-Myc.

Inhibitors of MMP2/Integrin $\alpha v \beta 3$ Interactions. Tumor growth is dependent on the formation of new blood vessels, a process termed angiogenesis. The early steps of angiogenesis involve the branching of endothelial cells from the existing vasculature, which requires remodeling of the vascular basal lamina and the extracellular matrix (ECM). Matrix metalloproteinases (MMPs) in the extracellular environment are responsible for breaking down the basal lamina and the ECM. Unfortunately, since MMPs have a broad range of functions in the adult organism, active-site inhibitors of MMPs possess damaging side effects, which limit their the clinical use as anti-angiogenic agents. Another therapeutic avenue toward the prevention of angiogenesis in tumors emerged when one family member, MMP-2, was found to associate with the integrin $\alpha v \beta 3$ on the surface of invasive angiogenic vascular cells and melanoma cells in vivo, and inhibition of the MMP-2/$\alpha v \beta 3$ interaction by a polypeptide comprising the $\alpha v \beta 3$-binding domain of MMP-2 was shown to disrupt angiogenesis. Hence, inhibition of the MMP-2/$\alpha v \beta 3$ interaction by small organic molecules may provide an alternative entry point for the treatment of cancer.

In an attempt to identify small-molecule inhibitors of MMP-2/$\alpha v \beta 3$ interactions as antiangiogenic agents, investigators monitored the interactions between MMP-2 and $\alpha v \beta 3$ in the presence of members of a chemical library. This library was synthesized by combining six different amines R1 with 10 different amines R2 through a iminodiacetic acid linker. Dimerization of each of the 60 single compounds with a mixture of 10 rigid dicarboxylic acids R3 provided 60 compound mixtures consisting of 10 different compounds each.

In the absence of precise structural information about the MMP2-$\alpha v \beta 3$ interface, binding between $\alpha v \beta 3$ and MMP-2 was analyzed in an enzyme-linked immunosorbent assay (ELISA). Purified $\alpha v \beta 3$ was first coated on the surface of a microtiter plate, followed by incubation of the immobilized $\alpha v \beta 3$ with biotinylated MMP-2 in the presence of the screening compounds. Finally, an anti-biotin antibody coupled to the enzyme horseradish peroxidase (HRP) was added, and the extent of MMP-2/$\alpha v \beta 3$ binding in the presence of the screening compounds was quantified colorimetrically by using an HRP substrate.

Deconvolution of active mixtures identified compound A6B10C4 as an inhibitor of the MMP-2/$\alpha v \beta 3$ interaction (79% inhibition at 3 µM compound). It is noteworthy that the enantiomer of this compound has no inhibitory activity, which demonstrates the importance of stereochemistry for the design of small-molecule modulators of protein-protein interactions. Structural optimization resulted in the identification of another compound and its simplified analogue, which was more suited for in vivo testing because of its improved solubility and lower molecular weight (IC50=1 µM for both compounds in the in vitro binding assay). Both of these latter compounds specifically bound to $\alpha v \beta 3$, not to MMP-2, in a dose-dependent manner. The ability of $\alpha v \beta 3$-infected melanoma cells to degrade the main constituent of the basal lamina (collagen IV) was inhibited by the simplified analogue in the low micromolar concentration range. The simplified analogue also inhibited angiogenesis and tumor growth in vivo without suppressing MMP-2 activation. The identification of the simplified analogue demonstrates the principal feasibility of targeting the MMP2/$\alpha v \beta 3$ interaction with small organic molecules, and raises hope that in the future aberrant angiogenesis in cancers may be treatable with drugs that cause less detrimental side effects.

Inhibitors of Binding of TNF-$\alpha$ to Its Receptor TNFRc1. The cytokine tumor-necrosis factor alpha (TNF-$\alpha$) plays an important role in the inflammatory response to tissue injury and various viral and bacterial infections. TNF-$\alpha$ forms homotrimers which bind to the TNF-$\alpha$ receptors 1 and 2 and induce receptor trimerization. Depending on the cellular context, trimerization of the TNF-$\alpha$ receptor 1 (TNFRc1) can lead to activation of the immune system by the NF-$\kappa$B signaling pathway. Since aberrantly increased TNF-$\alpha$ activity may also lead to tissue damage, inhibitors of TNF-$\alpha$ are of clinical interest for the treatment of autoimmune diseases, such as rheumatoid arthritis or Crohn's disease. These pathological conditions are currently being treated with anti-TNF-$\alpha$ antibodies and soluble receptor molecules, which act by sequestering TNF-$\alpha$. Inhibition of the interaction between TNF-$\alpha$ and its receptor TNFRc1 may be an alternative approach for inhibition of TNF-$\alpha$ activity.

Investigators set up a solid-phase binding assay to screen chemical libraries for antagonists of the TNF-$\alpha$/TNFRc1 interaction. To this end, the TNF-$\alpha$ receptor TNFRc1 was immobilized on microtiter plates, and binding of fluorescent-labeled TNF-$\alpha$ to its receptor was quantified in the presence of the screening compounds. The screen identified N-alkyl 5-arylalkylidene-2-thioxo-1,3-thiazolidin-4-ones as antagonists for the TNF-$\alpha$/TNFRc1 interaction. The most active compound IW927 inhibited the TNF-$\alpha$/TNFRc1 interaction with an apparent IC50 value of 50 nM and also blocked TNF-$\alpha$-stimulated phosphorylation of I$\kappa$B, an intermediate event in the activation of NF-$\kappa$B signaling. Surprisingly, the activity of the compounds decreased by up to 1000-fold when the binding assays were performed in the dark. Detailed X-ray crystallographic and other investigations of the binding mode of the analogue compound IV703 revealed that this inhibitor reversibly bound to TNFRc1 with only micromolar affinity in the absence of light. Under normal lighting conditions, the nitrophenyl ring of the analogue compound subsequently became covalently attached to the backbone nitrogen of an alanine residue of TNFRc1, thereby preventing the binding of TNF-$\alpha$ to its receptor. Since in a living organism activation of the compounds by light is not generally feasible, the activity of the compounds in the dark must be used to judge their utility. The data suggest that caution should be exercised when analyzing the biological activity of compounds containing an N-alkyl 5-arylalkylidene-2-thioxo-1,3-thiazolidin-4-one core.

Inhibitors of LFA-1/ICAM-1 Interactions. The binding of activated leukocyte function-associated antigen-1 (LFA-1) to its endothelial-cell-ligand intercellular adhesion molecule-1 (ICAM-1, CD54) is an important step in the migration of leukocytes from the bloodstream to the surrounding tissues during the early stages of inflammation. The integrin LFA-1, expressed on all leukocytes, consists of a large $\alpha L$ subunit (CD11a) and a small $\beta 2$ subunit (CD18) and is activated by exposure to cytokines and pro-inflammatory mediators. In addition to this role in the early stages of inflammation, the interaction between LFA-1 on the surface of T cells and ICAM-1 provides a strong costimulatory signal during T-cell activation. T-cell activation and proliferation is a crucial component of the immune response. Inhibitors of the LFA-1/ICAM-1 interaction consequently have the potential to inhibit both the inflammatory and the immune response. Inhibitors of the LFA-1/ICAM-1 interaction developed for the treatment of inflammatory diseases and graft rejection after transplantation have mostly been based on monoclonal antibodies directed against CD11a, the $\alpha$-chain of LFA-1. CD11a contains a multidomain $\beta$-propeller motif. Between two of the domains of the $\beta$-propeller, a domain referred to as the I-domain is inserted. Part of the I-domain is a magnesium-cation-binding domain, called the metal-ion-dependent adhesion site (MIDAS), which is directly involved in the interaction of CD11a with ICAMs.

Lovastatin, a drug clinically used for lowering cholesterol levels, was identified as an inhibitor of LFA-1/ICAM-1 interactions in an LFA-1-dependent adhesion assay. A lovastatin analogue, LFA703, with improved activity (IC50=200 nM in a solid-phase binding assay) was subsequently identified and found to suppress the inflammatory response in a mouse model of acute inflammation. LFA451 (IC50=40 nM) is the most active statin inhibitor of the LFA-1/ICAM-1 interaction identified to date. Investigators discovered the hydantoin BIRT 377 as a nanomolar antagonist for the LFA-1/ICAM-1 interaction by screening of proprietary chemical libraries and subsequent lead optimization. Interestingly, they report that the enantiomer of BIRT 377 is 35-times less potent, once again emphasizing the importance of stereoselective synthesis for the discovery of small-molecule modulators of protein-protein interactions. Other investigators identified p-arylthio cinnamides as antagonists for the LFA-1/ICAM-1 interaction, and performed extensive structure-activity relationship (SAR) studies using an NMR-spectroscopy-based model of the complex formed between the compounds and their LFA-1 binding site. This investigation ultimately resulted in the identification of a compound as a nanomolar inhibitor (IC50=6 nM in a solid-phase binding assay). This compound was shown to inhibit cell migration by blocking LFA-1/ICAM1 interactions in vivo, which suggests that it may reduce the severity of an in vivo inflammatory reaction.

Structural investigations indicated that none of the inhibitors mentioned above directly inhibit ICAM-1 binding by interacting with the MIDAS site of LFA-1. Instead, they bind to a site within the I-domain of LFA-1 with suggested regulatory function, thereby preventing an allosteric change required for LFA-1 to achieve a conformation that binds ICAM-1 with high affinity. This allosteric regulation of protein-protein interactions is an interesting approach as it circumvents potential difficulties encountered when targeting large, possibly discontinuous protein-protein interfaces with small molecules.

The most potent inhibitor of LFA-1/ICAM-1 interactions to date was identified by an approach involving rational design. The LFA-1 binding epitope of ICAM-1 consists of residues Glu 34, Lys 39, Met 64, Tyr 66, Asn 68, and Gln 73. Molecular modeling and alanine scanning identified the sequence motif Arg-Gly-Asp-Met-Pro as a mimic of the ICAM-1 residues Glu 34 and Lys 39. Analysis of disulfide-constrained, cyclized, heptapeptide libraries based on the Arg-Gly-Asp-Met-Pro epitope led to the identification of the inhibitor peptide H2N-Cys-Gly-Tyr(m)-Asp-Met-Pro-Cys-COOH (Tyr(m)=meta-tyrosine). During the course of these studies, ortho-bromobenzoyl tryptophan was identified as an inhibitor of the LFA-1/ICAM-1 interaction in independent investigations. Alignment of ortho-bromobenzoyl tryptophan with the C-terminus of H2N-Cys-Gly-Tyr(m)-Asp-Met-Pro-Cys-COOH suggested that a three-atom extension at the 4-position of the benzoyl ring of ortho-bromobenzoyl tryptophan could mimic the meta-phenol group of meta-tyrosine. In fact, such a compound is 30-times more active than ortho-bromobenzoyl tryptophan. Further optimization led to the discovery of another compound, which inhibited LFA-1/ICAM-1 interactions with an IC50 value of 1.4 nM in an in vitro binding assay. This compound was demonstrated to inhibit LFA-1-mediated lymphocyte proliferation and adhesion in vitro, and is equivalent to an anti-CD11a antibody in its potency of inhibition of the immune response in vivo. It is conceivable that this compound truly mimics the LFA-1 binding epitope of ICAM-1, since some of the functional groups of the LFA-1 binding epitope of ICAM-1 are also in this compound.

Inhibitors of iNOS Dimerization. Nitric oxide has been implicated in a wide range of physiological functions related to the central nervous system, the cardiovascular system, and the immune system. Nitric oxide is able to function as a rapidly reversible, specific, and local signal-transduction molecule, but also as a nonspecific mediator of tissue damage. Nitric oxide is synthesized from L-arginine by a family of enzymes, the nitric oxide synthases (NOS), through the arginine-nitric oxide pathway. NOS isoforms are enzymatically active only as homodimers. Since inducible nitric oxide synthase (iNOS) has been implicated in the pathogenesis of a number of inflammatory and autoimmune diseases, small-molecule inhibitors of iNOS are potentially of therapeutic use.

Based on previous observations that phenylimidazoles inhibit iNOS activity, investigators designed a structurally related chemical library containing a pyrimidineimidazole core. Screening of this library in a cell-based assay measuring NO production resulted in the identification of an iNOS inhibitor (IC50=1.1 nM). Surprisingly, this compound was unable to inhibit partially purified recombinant human iNOS in its natural dimeric form. Therefore, the investigators speculated that this compound inhibited the dimerization of iNOS monomers to enzymatically active homodimers. Indeed, size-exclusion chromatography of cellular extracts revealed that an inhibitor analogue inhibited the intracellular association of iNOS monomers. More importantly, an X-ray structure of this inhibitor analogue bound to the monomeric oxygenase domain of iNOS showed that it occupied the iNOS active site and thereby induced allosteric changes in the monomer which prevented the formation of stable homodimers. The most active compound (IC50=0.5 nM) was demonstrated to be a highly selective and cell-permeable research tool for the study of cellular iNOS functions. This example demonstrates once more that dimeric enzymes may be inhibited not only by active-site inhibitors, but also by inhibitors of enzyme subunit association.

Agonists of the EPO Receptor. The production of red blood cells is regulated by the hormone erythropoietin (EPO). Like other cytokines, EPO activates its receptor by binding to two receptor molecules which leads to receptor dimerization.

Binding of EPO, a 34 kDa glycoprotein, to the erythropoietin receptor (EPOr) leads to proliferation and differentiation of erythroid progenitors into red blood cells. In humans, EPO is primarily produced in the kidney, and anemias caused by kidney failure are currently treated with recombinant EPO. As EPO needs to be administered by repeated injection, orally administered small-molecule EPO mimics would be highly desirable.

While the inhibition of protein-protein interactions with a small molecule requires the molecule to bind to only one of the proteins in a fashion that inhibits the interactions between the two proteins, inducing the interactions between two proteins requires simultaneous binding of the small molecule to both proteins in a productive fashion. Inducing the dimerization of two EPO receptor molecules could hence be achieved by either a receptor-binding molecule which is displayed in two or multiple copies on a dendrimer, or by a symmetrical compound which uses only one set of its functional groups for binding one receptor molecule. Following the first approach, investigators identified a compound from a chemical library as a compound that binds to the EPO receptor. Subsequently, eight copies of this compound were arranged on a central core to allow for simultaneous binding of at least two EPO-binding molecules to the EPO receptor. This eight-copy compound binds to the EPO receptor with slightly higher affinity than the original compound (when calculated on a monomer basis), and in contrast to the original, is able to induce receptor dimerization in vitro (EC50=15.9 µM). This compound activates the EPO receptor in a manner similar to that of EPO itself; for example, it supports the proliferation of several tumor-cell lines expressing the EPO receptor and induces differentiation of human progenitor cells into colonies of erythrocytic lineage in tissue culture.

Following the second approach, other investigators screened a C2-symmetrical chemical library for molecules that bind to the EPO receptor. The same chemical library that was used in the search for inhibitors of MMP2/αvβ3 interactions was used in the primary screen for EPO-binding molecules, and the same compound A6B10C4 was identified, albeit with much lower affinity for its target. Structural optimization of this compound resulted in the discovery of compound A7B10C1 which inhibited binding of EPO to its receptor by 45% (at 50 µM) and increased proliferation of an EPO-dependent cell line by up to 175%. A similar compound, A1B10C1, was equally as active as the eight-copy compound at nanomolar concentrations, but has a significantly lower molecular weight. The data suggest that compounds A7B10C1 and A1B10C1 may act as weak partial agonists of the EPO receptor, although the possibility that the compounds affect alternative downstream targets cannot be ruled out.

Agonists for the Interaction Between Mutated Human Growth Hormone and Its Mutated Receptor. Human growth hormone (hGH) participates in the regulation of normal human growth and development. In a similar manner to the EPO-EPO receptor system, binding of hGH to its receptor leads to receptor dimerization and activation. The interaction between hGH and the extracellular domain of its receptor (hGHbp) has been extensively analyzed by approaches including X-ray-structural and mutational analysis. The discovery that a central region in the receptor, dominated by the two tryptophan residues Trp 104 and Trp 169, accounts for more than three quarters of the binding free energy was one of the landmarks of protein-protein interaction research, and led to the initial postulation of the hot spot theory. Investigators have used this interaction as a model system to design a small-molecule switch for protein-protein interactions. In the hGH/hGHbp complex, Trp 104 of hGHbp tightly packs against Thr 175 of hGH. Mutation of both residues to glycine reduced the binding affinity between hormone and receptor by a factor of $10^6$. A library of roughly 200 indole analogues was then screened for molecules that could restore the protein-protein interaction. 5-Chloro-2-trichloromethyl benzimidazole increased the binding affinity of the mutant hormone to the mutant receptor by more than 1000-fold at a concentration of 100 μM (Kd=260 nM). The mutated hormone-receptor pair mediated growth-hormone signaling in the presence of this compound. This example demonstrates that glycine mutations of amino acid side chains which significantly contribute to the overall binding free energy of a given protein-protein interaction can be partially compensated by small organic molecules possessing similar chemical features as the wild-type amino acid side chains.

Stabilization of Transthyretin Tetramers. Insoluble protein fibrils resulting from the self-assembly of a conformational intermediate are implicated as causative agents in several human amyloid diseases, including Alzheimer's disease, familial amyloid polyneuropathy, and senile systemic amyloidosis. The latter two diseases are caused by deposition of insoluble transthyretin (TTR) fibrils in the peripheral nerves and heart tissue. TTR, a tetrameric protein found in plasma and cerebral spinal fluid, binds to and transports thyroxine and the retinol binding protein. The formation of insoluble TTR amyloid fibrils requires as an intermediate step the dissociation of the TTR tetramer to monomers with altered tertiary structure. Studies by investigators showed that the TTR-ligand thyroxine inhibited TTR amyloid formation by stabilizing the TTR tetramer against dissociation, and thereby demonstrated that small organic molecules could be used to interfere with TTR-associated amyloid fibril formation. Since the hormonal activity of thyroxine-like molecules makes them undesirable as drugs, other small molecules which were thought to complement the binding site of TTR were screened for their ability to inhibit TTR amyloid fibril formation. The nonsteroidal anti-inflammatory drug (NSAID) flufenamic acid (FLU) was found to potently inhibit amyloid fibril formation in vitro. The X-ray structure of the FLU-TTR complex showed that two FLU molecules are bound to the TTR tetramer, and that FLU stabilizes the TTR tetramer by mediating intersubunit hydrophobic interactions and intersubunit hydrogen bonds. Further screening of chemicals, some of which were structurally related to FLU, indicated that good stabilization of TTR tetramers requires a molecule with at least two aromatic rings, one of which needs to carry an acidic functional group. Unfortunately, undesirable side effects known to accompany the prolonged use of FLU prevent its clinical use as an amyloidosis inhibitor. Screening of other NSAIDs showed that diclofenac (Voltaren), flurbiprofen, and resveratrol also strongly inhibited the formation of TTR amyloid fibrils in vitro. Detailed crystallographic investigations of the drug-TTR interactions and molecular modeling led to the development of the potent inhibitors of TTR fibril formation, ortho-trifluoromethylphenyl anthranilic acid (o-FLU) and N-(meta-trifluoromethylphenyl)-phenoxazine-4,6-dicarboxylic acid (PHENOX). The superior ability of PHENOX and other N-phenyl phenoxazine ligands to stabilize the TTR tetramer was confirmed by mass spectrometry studies. Furthermore, a diclofenac analogue was found to be potentially more suitable than diclofenac for the treatment of TTR-associated amyloidosis, as it was not only a potent inhibitor in vitro, but also partitioned more effectively than diclofenac into TTR in human plasma. These studies are an impressive demonstration of the ability of small organic ligands to interfere with amyloid fibril formation.

PHARMACEUTICAL MANUFACTURING

The discovery and development of new chemical entities (NCEs) into stable, bioavailable, marketable drug products is a long, but rewarding process. Due to the tremendous cost of developing a NCE, and industry's need to enhance productivity, it is desirable to create NCEs that have suitable physical-chemical properties, rather than compensate for deficiencies solely by the formulation process. Hence, property-based design can enhance the likelihood a NCE will have the desired physical-chemical properties that will facilitate its ability to be developed into a stable, bioavailable dosage form. Even so, well-designed preformulation studies are necessary to fully characterize molecules during the discovery and development process so that NCEs have the appropriate properties, and there is an understanding of the deficiencies that must be overcome by the formulation process.

With regard to solutions, emulsions, and suspensions, the dosage forms are prepared by employing pharmaceutically and therapeutically acceptable vehicles. The active ingredient(s) may be dissolved in aqueous media, organic solvent or combination of the two, by suspending the drug (if it is insoluble) in an appropriate medium, or by incorporating the medicinal agent into one of the phases of an oil and water emulsion.

The preparation of these dosage forms involves several considerations on the part of the pharmacist, namely, purpose of the drug, internal or external use, solubility and concentration of the drug, selection of the liquid vehicle(s), physical and chemical stability of the drug and any excipients, preservation of the preparation, and use of appropriate excipients such as buffers, solubility enhancers, suspending agents, emulsifying agents, viscosity controlling agents, colors and flavors. Oral preparations require consideration be given to improving patient compliance by making an acceptable product; consequently, color, odor and taste must be considered. The viscosity of a product also must be considered so that it has the proper palatability for an oral preparation and has the appropriate suspending properties if it is an emulsion or suspension. Because of the complexity of some manufactured products compounding may be carried out with the aid of linear programming models to obtain the optimal product.

Much has been written about the biopharmaceutical properties of solid dosage forms. Many researchers begin their absorption studies of drugs administered in solution to assess the bioavailability relative to tablets and capsules. Absorption occurs when drugs are in a dissolved state, thus it is frequently observed that the bioavailability of oral dosage forms decreases in the following order: aqueous solution>aqueous suspension>tablet or capsule. Formulation may influence the bioavailability and pharmacokinetics of drugs in solution, including drug concentration, volume of liquid administered, pH, ionic strength, buffer capacity, surface tension, specific gravity, viscosity and excipients. Emulsions and suspensions are more complex systems; consequently, the bioavailability and pharmacokinetics of these systems may be affected by additional formulation factors such as surfactants, type of viscosity agent, particle size and particle-size distribution, polymorphism and solubility of drug in the oil phase.

Liquid preparations maybe dispensed in one of three ways: (1) in its original container, (2) repackaging a bulk product at the time a prescription is presented by the patient or (3) compounding the solution, suspension, or emulsion in the dispensary. Compounding may involve nothing more than mixing marketed products in the manner indicated on the prescription or, in specific instances, may require the incorporation of active ingredients and excipients in a logical and pharmaceutically acceptable manner into aqueous or organic solvents that will form the bulk of the product.

Parenteral dosage forms differ from all other drug dosage forms because they are injected directly into body tissue through the primary protective system of the human body, the skin, and mucous membranes. They must be exceptionally pure and free from physical, chemical, and biological contaminants. These requirements place a heavy responsibility on the pharmaceutical industry to practice current good manufacturing practices (cGMPs) in the manufacture of parenteral dosage forms and upon pharmacists and other health care professionals to practice good aseptic practices (GAPs) in dispensing them for administration to patients.

Certain pharmaceutical agents, particularly peptides, proteins, and many chemotherapeutic agents, can only be given parenterally because they are inactivated in the gastrointestinal tract when given by mouth. Parenterally administered drugs are relatively unstable and generally highly potent drugs that require strict control of their administration to the patient. Because of the advent of biotechnology, parenteral products have grown in number and usage around the world.

Ophthalmic preparations are specialized dosage forms designed to be instilled onto the external surface of the eye (topical), administered inside (intraocular) or adjacent (periocular) to the eye. The preparations may have any of several purposes, therapeutic or prophylactic. Topical dosage forms have customarily been restricted to solutions, suspensions, and ointments.

In the formulation of a vehicle for application to the skin or various body orifices, many factors must be considered. Drug stability, intended product use, site of application, and product type must be combined in a dosage form or delivery system that will release the drug readily when placed in contact with the skin or body surface. Further, the release characteristics of the vehicle depend on the physical-chemical properties of the specific drug substance to be delivered to the skin or other surface: drug release from a vehicle is a function of the drug's concentration and solubility in the vehicle, and the drug's partition coefficient between the vehicle and the skin or body surface.

Drug substances most frequently are administered orally by means of solid dosage forms such as tablets and capsules. Large-scale production methods used for their preparation require the presence of other materials in addition to the active ingredients. Additives also may be included in the formulations to facilitate handling, enhance the physical appearance, improve stability, and aid in the delivery of the drug to the bloodstream after administration. These supposedly inert ingredients, as well as the production methods employed, have been shown in many cases to influence the absorption or bioavailability of the drug substances. Therefore, care must be taken in the selection and evaluation of additives and preparation methods to ensure that the drug-delivery goals and therapeutic efficacy of the active ingredient(s) will not be diminished.

In a number of cases it has been shown that the drug substance's solubility and other physicochemical characteristics have influenced its physiological availability from a solid dosage form. These characteristics include its particle size, whether it is amorphous or crystalline, whether it is solvated or nonsolvated, and its crystalline, or polymorphic form. After clinically effective formulations are obtained, such variations among dosage units of a given batch, as well as batch-to-batch differences, should be reduced to a minimum through proper in-process controls and good manufacturing practices.

Currently, most modified-release delivery systems fall into the following three categories: Delayed-release, extended-release, and site-specific targeting. Delayed-release systems are either those that use repetitive, intermittent dosing of a drug from one or more immediate-release units incorporated into a single dosage form, or an enteric delayed release system. Examples of delayed-release systems include repeat-action tablets and capsules, and enteric-coated tablets where time release is achieved by a barrier coating.

Extended-release systems include any dosage form that maintains therapeutic blood or tissue levels of the drug for a prolonged period. If the system can provide some actual therapeutic control, whether this is temporal or spatial or both, of drug release in the body, it is considered a controlled delivery system. This explains why extended-release is not equivalent to controlled-release.

Site-specific targeting refers to targeting a drug directly to a certain biological location. In the case of site-specific release the target is adjacent to or in the diseased organ or tissue. This system satisfies the special aspect of drug delivery requirements and is also considered a controlled drug delivery system.

Recently, a novel modification of drug delivery systems has emerged from the pharmaceutical industry. A fast-dissolve drug delivery system consists of a solid dosage form that dissolves or disintegrates in the oral cavity without the need of water or chewing. Among commercial products, fast dissolving or disintegration is achieved by forming an open matrix network containing the active ingredient (Zydis, Eli Lilly), by incorporating saliva-activated effervescent agents (OraSolv, Cima) or by using a mixture of a disintegrating agent and a swelling agent (Flashtab, Prographarm).

Inhalation therapy has been used for many years, and there has been a resurgence of interest in delivery of drugs by this route of administration. The number of new drug entities delivered by the inhalation route has increased over the past 5 to 10 years. This type of therapy also has been applied to delivery of drugs through the nasal mucosa, as well as through the oral cavity for buccal absorption. Originally, this type of therapy was used primarily to administer drugs directly to the respiratory system (treatment of asthma); inhalation therapy is now being used for drugs to be delivered to the bloodstream and finally to the desired site of action. Drugs administered via the respiratory system (inhalation therapy) can be delivered either orally or nasally. Further, these products can be developed as a nebulizer/atomizer, dry powder inhaler, nasal inhaler, or metered dose aerosol inhaler.

Although drugs differ widely in their pharmacodynamic effects and clinical applications; in penetration, absorption, and usual route of administration; in distribution among the body tissues; and in disposition and mode of termination of action, there are certain general principles that help explain these differences. These principles have both pharmaceutic and therapeutic implications. They facilitate an understanding of both the features that are common to a class of drugs and the differences among the members of that class. For a drug to act it must be absorbed, transported to the appropriate tissue or organ, penetrate to the responding cell surface or subcellular structure, and elicit a response or alter on-going processes. The drug may be distributed simultaneously or sequentially to a number of tissues, bound or stored, metabolized to inactive or active products, or excreted.

The dose of a drug required to produce a specified effect in 50% of the population is the median effective dose, abbreviated ED50. In preclinical studies of drugs, the median lethal dose, as determined in experimental animals, is abbreviated as the LD50. The ratio of the LD50 to the ED50 is an indication of the therapeutic index, which is a statement of how selective the drug is in producing the desired versus its adverse effects.

FLUORESCENCE-BASED ASSAYS TO IDENTIFY INHIBITORS OF THE IGE-RECEPTOR INTERACTION

Figure 1B:
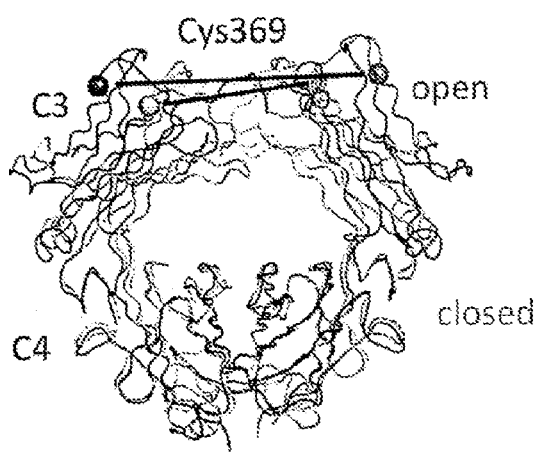
Figure 1C:
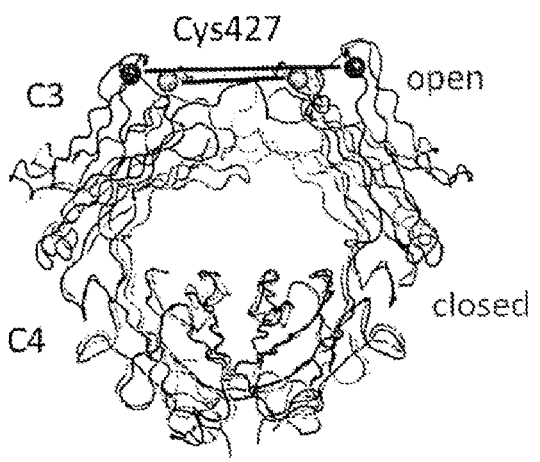

Our initial approach to devising a high-throughput fluorescence assay to measure IgE receptor binding was based on using fluorescence energy transfer (FRET) to monitor the IgE-Fc conformational change. For this FRET-based assay, IgE-Fc cysteine mutations were made at three sites, residue 367 (K367C), residue 369 (T369C) and residue 427 (R427C). These residues are located in IgE C3 loops near to the FcεRI binding site, but are not involved in receptor binding (FIG. 1). All three residues undergo large shifts (~15 Å) in the transition from the open to closed conformations (Wurzburg, B. A., Garman, S. C. & Jardetzky, T. S. 2000 *Immunity* 13: 375-385; Garman, S. C. et al. 2000 *Nature* 406: 259-266), with absolute distances close to the Förster radii (R0) for many standard FRET dye pairs (typically ~30-70 Å). These mutation sites are shown in FIG. 1 with the relative distances in the open and closed IgE-Fc conformations indicated.

Figure 2:
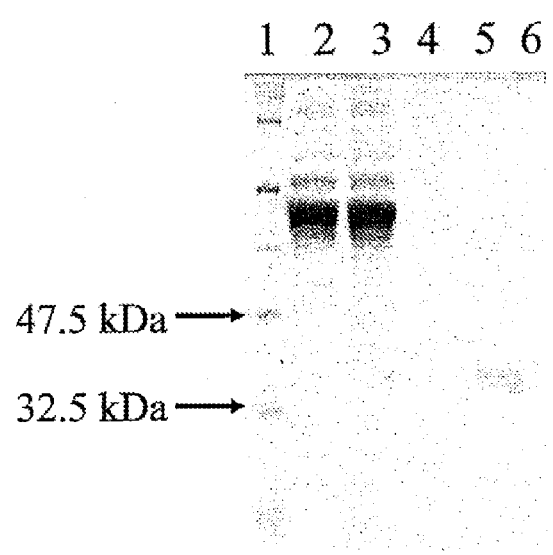
FIG. 2. Purification of the IgE-Fc C328A/K367C mutant.

The IgE-Fc mutants containing cysteines at positions 369 and 427 were not expressed and secreted well enough for further studies. Only the IgE cysteine mutation at position 367 was secreted efficiently. The K367C mutant was purified, but exhibited variable reduction of an interchain disulfide bond formed by residue C328, which is typically generated during biosynthesis and dimerization of the IgE-Fc. The purified K367C mutant is dimeric in solution, despite reduction of the 328 disulfide bond, indicating that the dimer is stabilized predominantly by noncovalent interactions. The data indicated unexpectedly that the presence of the cysteine at residue 367 leads to reduction of the interchain disulfide bond. The reduction of the 328 disulfide bond was problematic for our assay development, since this could lead to heterogeneous labeling at both 328 and 367. We therefore generated a secondary mutation in the K367C protein, changing the cysteine at position 328 to alanine to generate a double mutant, removing the exposed interchain disulfide bond (C328A/K367C). The presence of the disulfide bond at residue 328 does affect the binding affinity of IgE-Fc to FcεRIα, but its removal only reduces the affinity of the interaction by a factor of ~10 fold (Basu, M. et al. 1993 *J Biol Chem* 268: 13118-13127). Since the natural receptor interaction is of high affinity (~1 nM), a 10-fold reduction in binding affinity still represents a high affinity interaction and it would have the added benefit of making the interaction easier to compete with a low affinity lead inhibitor. The double mutant, referred to as 367C IgE-Fc, was purified from insect cell supernatants (FIG. 2) and doubly labeled with the Alexa Fluor 350 and Alexa Fluor 488 dye pair (R0=50 Å) (Molecular Probes, Table 1.6—RO values for some Alexa Fluor dyes. 2009, http://probels.invitrogen.com/handbook/R0-values-for-some-Alexa-Fluor-dyes.html) for initial FRET experiments.

The Binding of Receptor to Labeled IgE-Fc Quenches Dye Fluorescence

Figure 3:
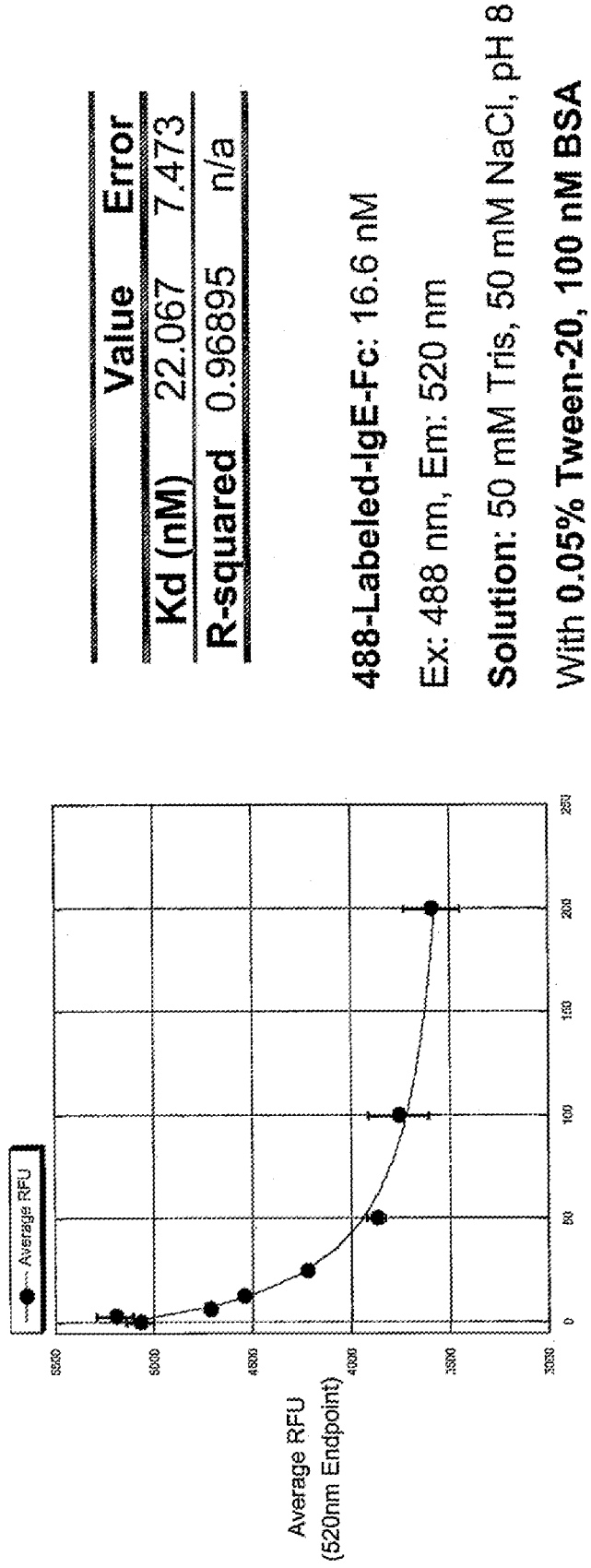
FIG. 3. Fluorescence quenching measures the binding of receptor to the labeled IgE-Fc.

In preliminary FRET experiments it became apparent that receptor binding might be quenching dye fluorescence independently of the observed FRET signals. The 367C IgE-Fc was labeled separately with the Alexa fluor 350 (350-labeled 367C IgE-Fc) and the Alexa fluor 488 (488-labeled 367C IgE-Fc) in order to investigate this possibility. Systematic fluorescence quenching was observed from both of these singly dye-labeled proteins in the presence of FcεRIα. The 488-labeled 367C IgE-Fc provided a relatively higher fluorescence quenching signal when bound to FcεRIα (FIG. 3). Thus, the Alexa fluor 488 was chosen for the measurement of fluorescence quenching and receptor binding.

Binding buffer conditions were optimized to improve reproducibility of the binding assay in a 96-well plate format. A typical receptor binding titration is shown in FIG. 3, providing an estimated Kd value for the interaction of ~22 nM. This binding constant is within the expected range for the IgE-Fc lacking the C328 disulfide bond, consistent with our expectations.

Mechanism of Dye Quenching by Receptor Binding

Figure 4:
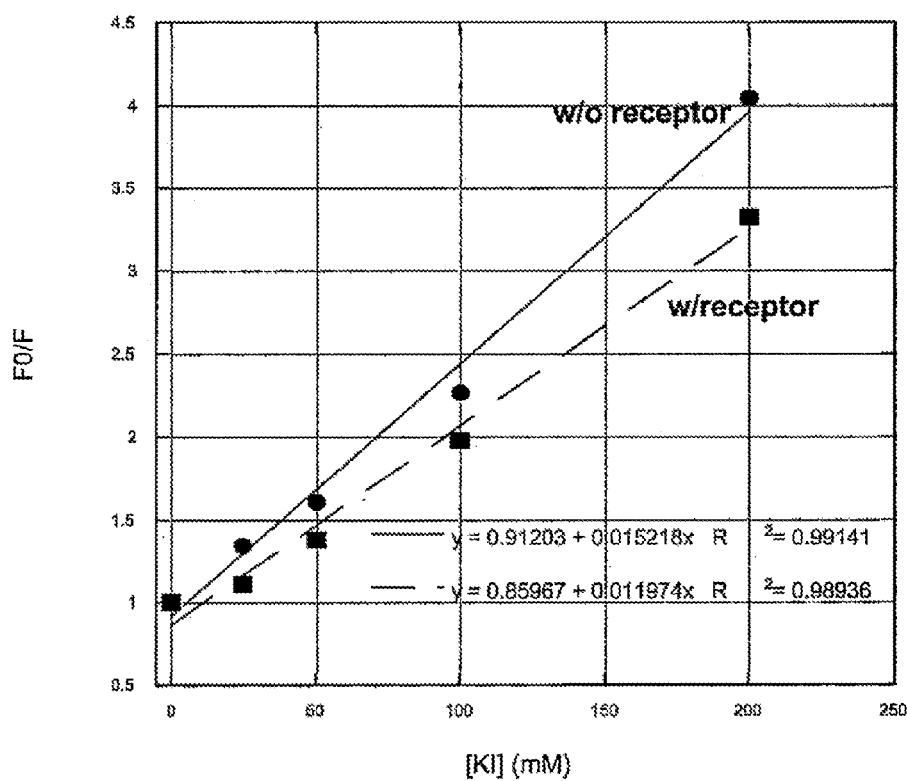
FIG. 4. Stern-Volmer analysis of the accessibility of dye labeled IgE-Fc in the presence and absence of receptor.

To better understand the fluorescence quenching observed in the binding of 488-labeled 367C IgE-Fc to FcεRIα, we performed experiments to probe the accessibility of the fluorescent dye in the bound and unbound states. The 488-labeled 367C IgE-Fc and the labeled IgE-Fc bound to FcεRIα were incubated with increasing concentrations of quenching agent (Iodide or KI) and the fluorescence intensity measured. The data were used to generate Stern-Volmer plots (FIG. 4). The slope of the relative intensity changes observed with increasing quenching agent (KI) indicates the extent of the accessibility of fluorescent dyes to the quencher (Shashidhara, K. S. & Gaikwad, S. M. 2007 *J Fluoresc* 17: 599-605).

The fluorescence of the free IgE-Fc is quenched more readily than the IgE-Fc bound to FcεRIα (FIG. 4), indicating that the dye label in the absence of FcεRIα is more accessible to quencher. The labeling site at residue 367 is not directly involved in the receptor binding interface, but is in a neighboring loop that can adopt different conformations, as observed in multiple crystal forms of the IgE-Fc. Based on this, we conclude that the IgE-receptor interaction likely causes a local conformational change (Wurzburg, B. A., Garman, S. C. & Jardetzky, T. S. 2000 *Immunity* 13: 375-385; Garman, S. C. et al. 2000 *Nature* 406: 259-266) in the IgE-Fc 367 loop that decreases the accessibility of dye label at position 367, resulting in a decrease in fluorescence intensity.

Quantitative Measurements of Inhibitors of IgE Binding

To demonstrate that the fluorescence assay is specific and can quantitatively follow the binding of inhibitors of the interaction, we measured the fluorescence of 488-labeled 367C IgE-Fc bound to FcεRIα in the presence of known competitors. In a competitive inhibitor format, the assay monitors inhibitor binding as increases in fluorescence intensity; competitors should have the effect of decreasing the fluorescence quenching by receptor.

Figure 5:
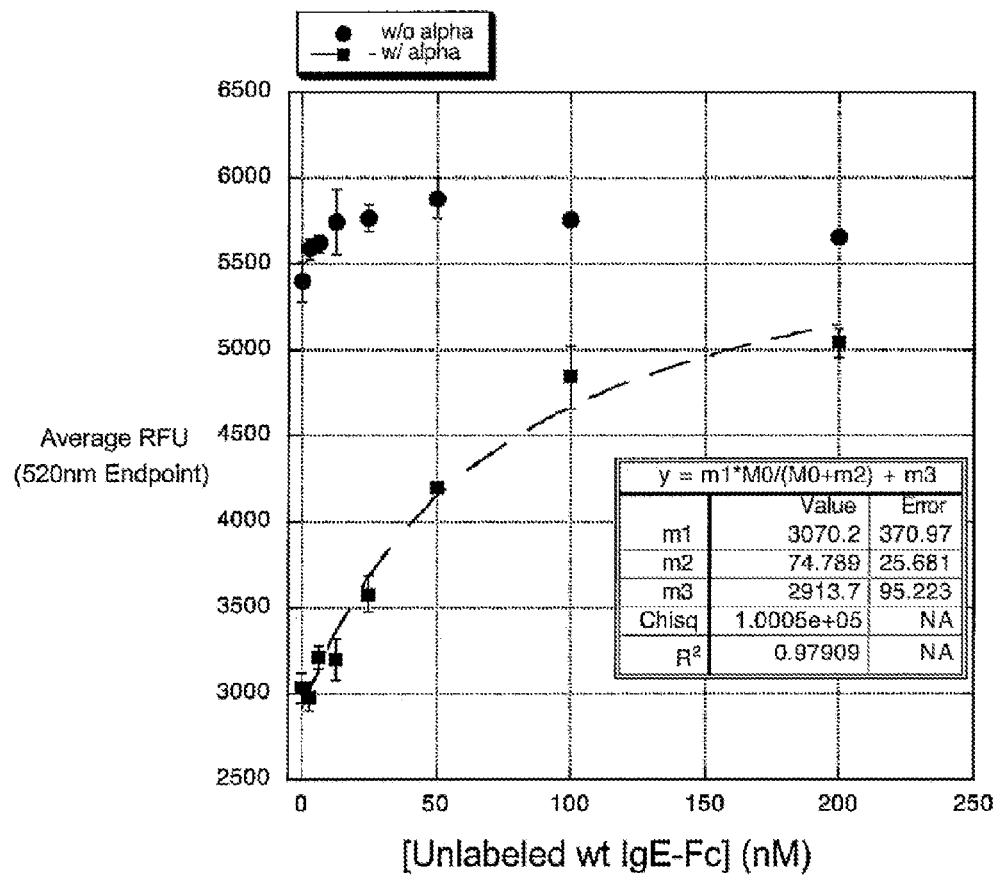
FIG. 5. Competition of binding observed with unlabeled wild type IgE-Fc.

Initial experiments were conducted with unlabeled IgE-Fc as the competitor. The unlabeled IgE-Fc exhibited the expected fluorescence recovery, decreasing the effect of fluorescence quenching induced by the receptor (FIG. 5). To ensure that the unlabeled IgE-Fc had no direct effect on the fluorescence signal of the dye-labeled IgE-Fc, parallel control experiments were conducted in the absence of FcεRIα (FIG. 5). These data showed that unlabeled IgE-Fc had no significant effect on the fluorescence of the dye-labeled IgE-Fc. The results indicate that the change in fluorescence reliably represents the relative extent of the interaction of the labeled IgE-Fc with FcεRIα, and that this can be completely competed with unlabeled IgE. An apparent $EC_{50}$ can be measured from the inhibition curve (EC50: ~75 nM).

Figure 6:
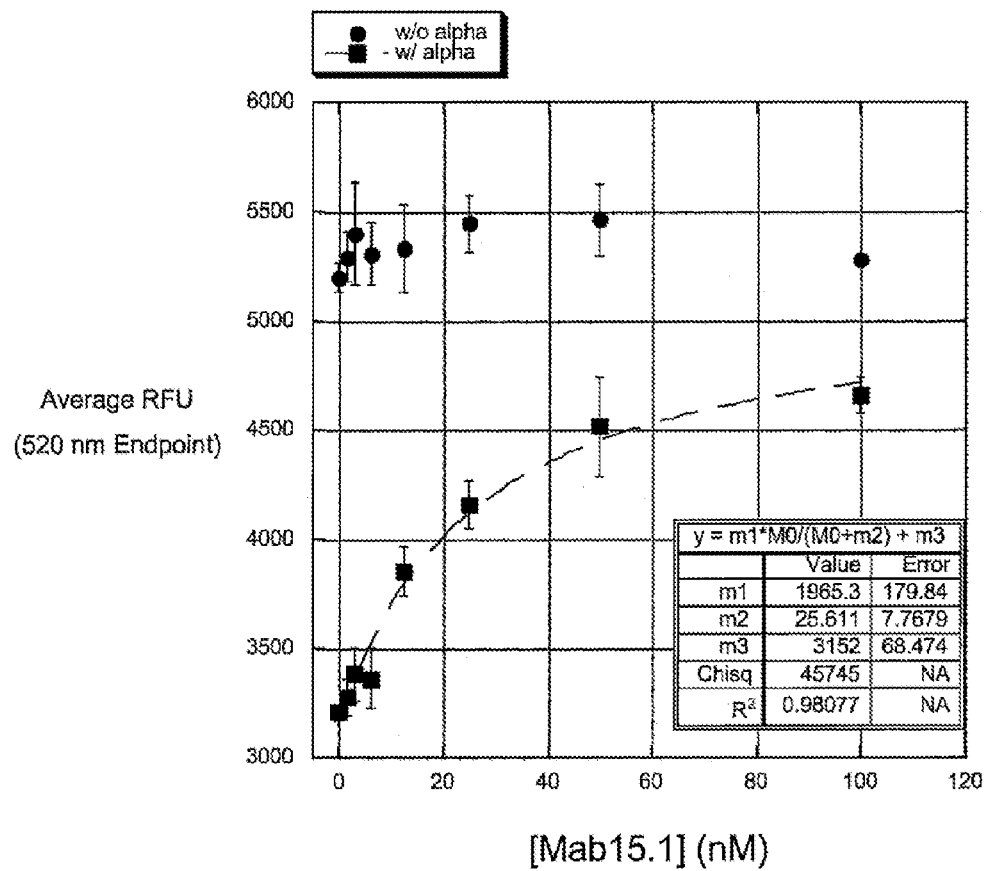
FIG. 6. Competition observed with anti-FcεRIα antibody Mab 15.1.

We further tested the ability of this assay to measure inhibition mediated by anti-receptor and anti-IgE antibodies. Mab 15.1 is a monoclonal antibody that binds to the α chain of FcεRIα and inhibits the IgE-receptor interaction (Mirkina, I., Schweighoffer, T. & Kricek, F. 2007 *Immunol Lett* 109: 120-128; Wang, B. et al. 1992 *J Exp Med* 175: 1353-1365). In the fluorescence assay, Mab 15.1 attenuates the fluorescence quenching, indicating that it competes with the binding of FcεRIα bound to the labeled IgE-Fc (FIG. 6). The control experiments conducted in the absence of FcεRIα demonstrate that Mab 15.1 has no direct effect on fluorescence of the labeled IgE-Fc. The apparent EC50 for the Mab 15.1 interaction is ~25 nM.

Figure 7:
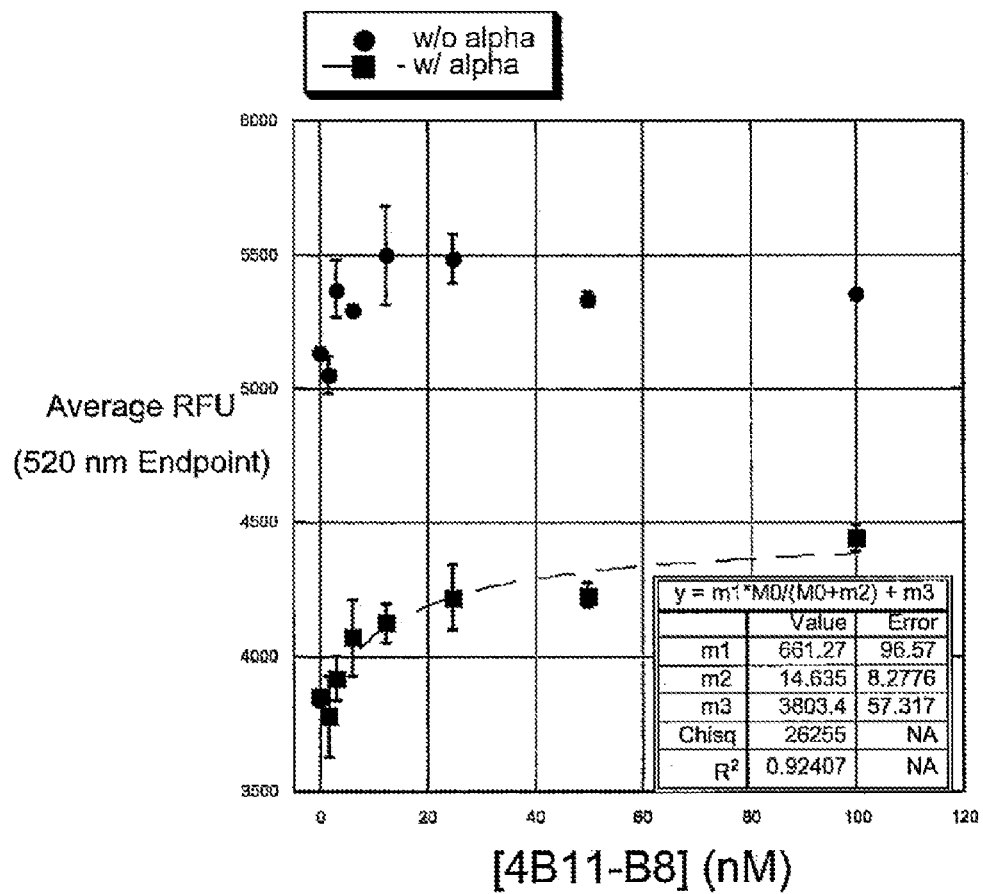
FIG. 7. Competition observed with the anti-IgE antibody, 4B11-B8.

4B11-B8 is an anti-IgE antibody isolated in our laboratory that competes for receptor binding and appears to bind at a site distant from the receptor binding site. Including purified 4B11-B8 protein in the assay as a competitor also led to increases in fluorescence (FIG. 7), although the extent of the recovery is lower when compared to Mab 15.1 (FIG. 6). The apparent EC50 for the interaction is 14 nM. The limited recovery of fluorescence indicates that 4B11-B8 may reduce the affinity of receptor binding, but not completely block the interaction.

We describe a simple, rapid, and sensitive fluorescence-based assay to detect the binding of IgE to the high affinity receptor (FcεRI), and further demonstrate that it can be used to quantitatively measure competitors of the binding interaction. This assay represents a simple "mix-and-read" assay conducted in a microplate format that is compatible with low-volume, high throughput screening methods. Due to the high sensitivity of the fluorescence signal of this assay, only small amounts of labeled IgE-Fc are required for the experiments, which will facilitate the screening of large libraries of potential inhibitors. In addition, since the IgE modifications, such as the removal of the wild type cysteine at residue 328 and the introduction of dye label in the IgE-Fc 367 loop, reduce the binding affinity of IgE-Fc to FcεRIα, this is envisioned and recognized as improving the ability of our assay to identify low, not only high, affinity lead inhibitors of the IgE-receptor interaction.

EXAMPLE 1

Material. Cysteine-reactive fluorescent dyes, Alexa Fluor 350 and Alexa Fluor 488, were purchased from Invitrogen/Molecular Probes.

Mutagenesis. Each mutation (K367C, T369C, and R427C) was introduced into the wild-type IgE-Fc gene, encoding the Cε3-Cε4 domains of human IgE-Fc, by site-directed mutagenesis (QuickChange kit: Stratagene), respectively. The mutagenic primer for the K367C change is: "K367C" 5'-GACCTGGCACCCAGC-TGT-GGGACCGTGAAC-CTG-3' (SEQ ID NO:11). A secondary mutation (C328A) was introduced into the mutant (K367C) by Mutagenex Inc. The mutagenic primers for the T369C and R427C change are the following: "T369C" 5'-GCACCCAGCAAGGGG-TGT-GTGAACCTGACCTGG-3' (SEQ ID NO:12) and "R427C" 5'-CACCCCCACCTGCCC-TGT-GCCCTCATGCGCTCC-3' (SEQ ID NO:13). The mutations were confirmed by DNA sequencing. We refer to the resulting double 328A/367C mutant protein as 367C IgE-Fc.

Expression, Purification, and Fluorescent Labeling of 367C IgE-Fc. The 367C IgE-Fc was cloned into pENTR1A (Invitrogen) and transferred into the BaculoDirect C-term Linear DNA by using LR Clonase II Enzyme Mix (Invitrogen). Recombinant baculovirus expressing the mutant was generated using BaculoDirect C-term Transfection Kit (Invitrogen). Recombinant virus was selected and amplified following standard protocols supplied by the manufacturer. The purified mutant includes 3 non-wild-type residues generated by the construct (ADP) at the N-terminus and 48 non-wildtype residues with a V5 epitope and a histidine affinity tag (His-tag) at the C-terminus. Refer to FIG. 8 for the nucleotide and amino acid sequence of the wild-type and mutant clones.

The 367C IgE-Fc protein was expressed and purified from insect cells (Trichoplusia ni). Supernatants were harvested 2.5-3 days post-infection and filtered through a Durapore 0.45 μM filter (Millipore). The supernatant was incubated with Ni-NTA agarose (Invitrogen) at room temperature for 3 hours, and then loaded into a column. The column was rinsed with 4-5 column volumes of the washing buffer (60 mM Sodium Phosphate, 50 mM Imidazole, and 300 mM NaCl, pH 7.5), and the mutant was eluted directly with the elution buffer (60 mM Sodium Phosphate, 200 mM Imidazole, and 300 mM NaCl, pH 7.5). The sample was dialyzed and concentrated using an Amicon ultrafiltration device (Millipore) into a final buffer consisting of 50 mM Tris and 50 mM NaCl, pH 8, at a protein concentration of 1 mg/ml$^{-1}$. Protein was quantified by absorbance at 280 nm, assuming the extinction coefficient of the mutant to be equivalent to the wild type protein (e=1.32 cm$^{-1}$(mg/ml)$^{-1}$) (Wurzburg, B. A., Garman, S. C. & Jardetzky, T. S. 2000 Immunity 13: 375-385).

The concentrated mutants were incubated with TCEP (Uptima), at 3 times the molar amount of the mutant, for 1 hour at room temperature. Subsequent to the treatment with TCEP, the presence of free thiol groups in the 367C mutant was confirmed by using the Thiol and Sulfide Quantitation Kit (Molecular Probes). For 367C IgE-Fc labeling with Alexa Fluor 488, the mutant was labeled using the maleimide derivative of the dye8, incubated at a 5 times molar excess over the mutant, at 4° C. overnight. Unreacted dye was removed by separation over a Superdex 200 column (GE Healthcare) equilibrated in 50 mM Tris, 50 mM NaCl, pH 8.

IgE Receptor Expression and Purification. The expression and purification of the human FcεRIα protein is described in Garman, S. C., Kinet, J. P., & Jardetzky, T. S. 1998 Cell 95:951-961.

4B11-B8. Refer to FIG. 9 for the nucleotide and amino acid sequence of the light and heavy chains of the 4B11-B8 FAb.

Fluorescence Measurement. Samples were monitored by fluorescence using a Synergy 4 Fluorometer (BioTek) in black 96-well Costar fluorescence plates (Corning). Samples were prepared manually by mixing Alexa-488-labelled 367C IgE-Fc in 0.1% Tween-20 and 100 nM BSA, with buffered 50 mM Tris and 50 mM NaCl, pH 8. Fluorescence was measured using an excitation wavelength of 488 nm and emission was monitored at 520 nm. The read-type for typical measurements was Endpoint. All measurements were recorded in duplicate.

The fluorescence data to assess dye accessibility analysis was obtained in the presence of quencher (Iodide or KI) and was analyzed using the Stern-Volmer equation (Eq. 1) (Xing, D., Don, R., Cunningham, R. P. & Scholes, C. P. 1995 Biochemistry 34: 2537-2544.).

$$F_0/F_c = 1 + K_{sv}[Q] \quad [1]$$

Where $F_0$ and $F_c$ are the relative fluorescence intensities in the absence and presence of the quencher, [Q] is the quencher concentration, and $K_{sv}$ is Stern-Volmer quenching constant.

These examples and embodiments are illustrative and are not to be read as limiting the scope of the invention as it is defined by this specification and the appended claims.

All references cited in this specification are incorporated herein by reference.

What is claimed is:

1. A polypeptide comprising an amino acid sequence that is at least identical to the amino acid sequence of a human IgE-Fc Cϵ3-Cϵ4, wherein said Cϵ3-Cϵ4 starts at amino acid 328 and ends at amino acid 547 of said IgE-Fc, using the numbering according to the reference sequence of SEQ ID NO:14, and wherein C 328 is an amino acid other than C and K 367 is C, and wherein the polypeptide is capable of binding to an FcϵRIα.

2. A polypeptide comprising the amino acid sequence of a human IgE-Fc Cϵ3-Cϵ4, wherein said Cϵ3-Cϵ4 starts at amino acid 328 and ends at amino acid 547 of said IgE-Fc, using the numbering according to the reference sequence of SEQ ID NO:14, but with up to 30% insertions, deletions, or conservative substitutions, and wherein C 328 is an amino acid other than C and K 367 is C, and wherein the polypeptide is capable of binding to an FcϵRIα.

3. The polypeptide of claim 1 comprising the amino acid sequence of a human IgE-Fc Cϵ3-Cϵ4, wherein said Cϵ3-Cϵ4 starts at amino acid 328 and ends at amino acid 547 of said IgE-Fc, using the numbering according to the reference sequence of SEQ ID NO:14, and wherein C 328 is an amino acid other than C and K 367 is C.

4. The polypeptide of claim 1, wherein said polypeptide binds to a FcϵRIα with a dissociation constant ($K_d$) of less than or equal to $10^{-8}$ M.

5. A polypeptide comprising the amino acid sequence of a human IgE-Fc Cϵ3-Cϵ4, wherein said Cϵ3-Cϵ4 starts at amino acid 328 and ends at amino acid 547 of said IgE-Fc, using the numbering according to the reference sequence of SEQ ID NO:14, and wherein C 328 is A and K 367 is C.

6. The polypeptide of claim 1, wherein said IgE-Fc Cϵ3-Cϵ4 sequence is labeled with a fluorophore.

7. The polypeptide of claim 1, wherein the polypeptide is capable of binding to a human FcϵRIα extracellular region with a dissociation constant ($k_d$) of less than $10^{-5}$ M.

8. The polypeptide of claim 7, wherein the $k_d$ is less than $10^{-6}$ M.

9. The polypeptide of claim 8, wherein the $k_d$ is less than $10^{-7}$ M.

10. The polypeptide of claim 9, wherein the $k_d$ is less than $10^{-8}$ M.

11. The polypeptide of claim 9, wherein the $k_d$ is less than or equal to 22 nM.

12. The polypeptide of claim 1, wherein the polypeptide comprises the amino acid sequence of SEQ ID NO:3.

13. The polypeptide of claim 1, wherein the polypeptide comprises an amino acid having at least 70% identity to the sequence of SEQ ID NO:3, wherein the polypeptide is capable of binding to an FcεRIα.

14. The polypeptide of claim 1, wherein the polypeptide comprises an amino acid having at least 95% identity to the sequence of SEQ ID NO:3, wherein the polypeptide is capable of binding to an FcεRIα.

15. A mixture comprising the polypeptide of claim 1 in admixture with a second polypeptide comprising an amino acid sequence that is at least 70% identical to the amino acid sequence of a human FcεRIα extracellular region, wherein said extracellular region starts at amino acid 1 and ends at amino acid 176 of said FcεRIα, using the numbering −25 to 232 according to the reference sequence of SEQ ID NO:15, and wherein the second polypeptide is capable of binding to the polypeptide of claim 1.

16. A mixture comprising the polypeptide of claim 1 in admixture with a second polypeptide comprising the amino acid sequence of a human FcεRIα extracellular region, wherein said extracellular region starts at amino acid 1 and ends at amino acid 176 of said FcεRIα, using the numbering −25 to 232 according to the reference sequence of SEQ ID NO:15, but with up to 30% insertions, deletions, or conservative substitutions, and wherein the second polypeptide is capable of binding to the polypeptide of claim 1.

17. The mixture of claim 15, wherein said second polypeptide mediates high affinity binding to an IgE-Fc, wherein the dissociation constant ($k_d$) is less than or equal to $10^{-8}$ M.

18. A mixture comprising the polypeptide of claim 1 in admixture with a second polypeptide comprising the amino acid sequence of a human FcεRIα extracellular region, wherein said extracellular region starts at amino acid 1 and ends at amino acid 176 of said FcεRIα, using the numbering −25 to 232 according to the reference sequence of SEQ ID NO:15.

19. A method of identifying a compound that inhibits the binding of an IgE-Fc to a FcεRIα, said method comprising:
   a. Contacting the polypeptide of claim 1, wherein said IgE-Fc Cε3-Cε4 sequence is labeled with a fluorophore, and a second polypeptide, with a test compound, said second polypeptide comprising an amino acid sequence that is at least 70% identical to the amino acid sequence of a human FcεRIα extracellular region, wherein said extracellular region starts at amino acid 1 and ends at amino acid 176 of said FcεRIα, using the numbering −25 to 232 according to the reference sequence of SEQ ID NO:15 and wherein the second polypeptide is capable of binding to the polypeptide of claim 1; and
   b. Determining whether binding of said polypeptide to said second polypeptide is decreased in the presence of said test compound, a decrease in said binding being an indication that the test compound inhibits the binding of said polypeptide to said second polypeptide.

20. The method of claim 19, wherein said decrease in binding is indicated by analysis of fluorescence polarization, FRET, or fluorescence intensity.

21. The method of claim 20, wherein said decrease in binding is mediated by competitive inhibition.

* * * * *